United States Patent
Minami et al.

(10) Patent No.: US 9,487,592 B2
(45) Date of Patent: Nov. 8, 2016

(54) IMMOBILIZATION SUBSTRATE AND METHOD FOR PRODUCING THE SAME

(75) Inventors: Koichi Minami, Ashigarakami-gun (JP); Hirohiko Tsuzuki, Ashigarakami-gun (JP); Hiroshi Ueda, Bunkyo-ku (JP); Masaki Ihara, Bunkyo-ku (JP)

(73) Assignees: FUJIFILM Corporation, Tokyo (JP); THE UNIVERSITY OF TOKYO, Tokyo (JP)

( * ) Notice: Subject to any disclaimer, the term of this patent is extended or adjusted under 35 U.S.C. 154(b) by 812 days.

(21) Appl. No.: 13/125,478

(22) PCT Filed: Oct. 23, 2009

(86) PCT No.: PCT/JP2009/068638
§ 371 (c)(1),
(2), (4) Date: Apr. 21, 2011

(87) PCT Pub. No.: WO2010/047419
PCT Pub. Date: Apr. 29, 2010

(65) Prior Publication Data
US 2011/0236679 A1    Sep. 29, 2011

(30) Foreign Application Priority Data

Oct. 24, 2008  (JP) ................................. 2008-274852
Nov. 18, 2008  (JP) ................................. 2008-294527
May 13, 2009  (JP) ................................. 2009-117080

(51) Int. Cl.
*C07K 16/18*      (2006.01)
*C07K 16/40*      (2006.01)

(52) U.S. Cl.
CPC ............... *C07K 16/40* (2013.01); *C07K 16/18* (2013.01); *C07K 2317/56* (2013.01); *Y10T 428/269* (2015.01)

(58) Field of Classification Search
None
See application file for complete search history.

(56) References Cited

U.S. PATENT DOCUMENTS

| | | | |
|---|---|---|---|
| 6,372,425 B1 * | 4/2002 | Arnold et al. | 506/2 |
| 2003/0049870 A1 | 3/2003 | Glad et al. | |
| 2005/0003560 A1 * | 1/2005 | Zeng et al. | 436/527 |
| 2006/0034845 A1 * | 2/2006 | Silence et al. | 424/145.1 |
| 2006/0105470 A1 * | 5/2006 | Jordan et al. | 436/514 |
| 2006/0252028 A1 * | 11/2006 | Ueda et al. | 435/5 |

(Continued)

FOREIGN PATENT DOCUMENTS

| | | |
|---|---|---|
| EP | 2 224 241 A1 | 9/2010 |
| JP | 06-510474 A | 11/1994 |
| JP | 10-078436 A | 3/1998 |

(Continued)

OTHER PUBLICATIONS

Klonisch (1996) Immunology 89: 163-171.*

(Continued)

*Primary Examiner* — Chris L Chin
*Assistant Examiner* — Richard Moerschell
(74) *Attorney, Agent, or Firm* — Sughrue Mion, PLLC

(57) ABSTRACT

An antibody-fragment-immobilizing substrate includes a substrate and at least one set of antibody fragments, wherein the antibody fragments of each set includes at least two types of separate antibody fragments that are capable of recognizing one type of antigen and that are independently immobilized on the substrate in a positional relationship that allows each of the antibody fragments in one set to bind to the same antigen.

7 Claims, 2 Drawing Sheets

(56) References Cited

U.S. PATENT DOCUMENTS

| | | | |
|---|---|---|---|
| 2007/0054417 A1* | 3/2007 | Odefey | 436/524 |
| 2007/0298510 A1 | 12/2007 | Imamura et al. | |

FOREIGN PATENT DOCUMENTS

| | | | | |
|---|---|---|---|---|
| JP | 2002502585 A | | 1/2002 | |
| JP | 3527239 B2 | | 2/2004 | |
| JP | 2006-137805 A | | 6/2006 | |
| JP | 2007278748 A | | 10/2007 | |
| JP | 4036961 B2 | | 11/2007 | |
| SE | WO 93/05068 | * | 3/1993 | C07K 3/18 |
| SE | WO 93/50068 | * | 3/1993 | C07K 3/18 |
| WO | 9925739 A1 | | 5/1999 | |
| WO | 2004/016782 A1 | | 2/2004 | |
| WO | 2006/033413 A1 | | 3/2006 | |
| WO | 2007023915 A1 | | 3/2007 | |

OTHER PUBLICATIONS

Saerens (2008) Sensors 8: 4669-4686.*

First Office Action, dated Apr. 15, 2013, issued in corresponding CN Application No. 200980142052.X, 13 pages in English and Chinese.

Communication Pursuant to Article 94(3) EPC, dated Apr. 29, 2013, issued in corresponding EP Application No. 09822111.2, 5 pages.

Ueda, Hiroshi, "Sensitive Noncompetitive Measurement of Small Molecules by Open Sandwich Immunoassay," Yakugaku Zasshi, 2007, pp. 71-80, vol. 127, No. 1.

Ueda, Hiroshi, "Open Sandwich Immunoassay: a Novel Immunoassay Approach Based on the Interchain Interaction of an Antibody Variable Region," Journal of Bioscience and Bioengineering, 2002, pp. 614-619, vol. 94, No. 6.

Liparoto, Stefano F., et al., "Biosensor analysis of the interleukin-2 receptor complex," Journal of Molecular Recognition, 1999, pp. 316-321, vol. 12.

Notice of Reasons for Rejection, dated Dec. 18, 2012, issued in related JP Application No. 2009244485, 7 pages in English and Japanese.

Communication, dated May 16, 2012, issued in corresponding EP Application No. 09822111.2, 7 pages.

Klonisch et al., "Enhancement in antigen binding by a combination of synergy and antibody capture," Immunology, vol. 89, No. 2, Oct. 1, 1996, pp. 165-171, XP55026485.

Saerens et al., "Antibody Fragments as Probe in Biosensor Development," Sensors, vol. 8, No. 8, Aug. 8, 2008, pp. 4669-4686, XP55026503.

Klonisch et al., "Relative location of epitopes involved in synergistic antibody binding using human chorionic gonadotropin as a model," European Journal of Immunology, vol. 26, No. 8, Aug. 1, 1996, pp. 1897-1905, XP55026526.

Office Action dated Apr. 2, 2014, issued by the European Patent Office in counterpart European Patent Application No. 09822111.2.

* cited by examiner

IMMOBILIZATION SUBSTRATE AND METHOD FOR PRODUCING THE SAME

TECHNICAL FIELD

The invention relates to an immobilization substrate and a method for producing the immobilization substrate.

BACKGROUND ART

Recently, a large number of measurements using intermolecular interactions such as immune responses are being carried out in clinical tests or the like. Among these, several techniques are preferably used that do not require a complicated operation or a labeled material but are capable of detecting the change in the binding amount of a test substance with high sensitivity. Examples of such techniques include a surface plasmon resonance (SPR) measurement technique, a quartz crystal microbalance (QCM) measurement technique, and a measurement technique using functional surfaces ranging from gold colloid particles to ultrafine particles. In any of these techniques, the surface on which a substance to be measured is immobilized is important. Hereinafter, the surface plasmon resonance (SPR) measurement technique will be described as an example.

In general, a measurement chip used for measuring a target substance includes a chip in which an evaporated metal film and a thin film having a functional group capable of immobilizing a target substance are formed on a transparent substrate (e.g., glass) in this order. The target substance is immobilized on the surface of the metal film via the functional group. The interaction between substances is analyzed by measuring a specific binding reaction between the target substance and a test substance.

However, the interaction between the target substance and the test substance, which occurs only when a substance assisting the interaction between the target substance and the test substance is present, cannot be directly detected by the method described above. In order to detect such an interaction between the target substance and the test substance, the test substance and an auxiliary substance are required to be simultaneously supplied to the target substance so that the auxiliary substance makes contact with the test substance or the target substance. For this reason, not only is a large amount of the auxiliary substance required, but also the cost of measurement is affected if it is difficult to obtain the auxiliary substance.

In addition, since the auxiliary substance, test substance and target substance are required to be located adjacent to one another, there has also been a problem in that the reaction efficiency decreases.

Moreover, the auxiliary substance includes not only a substance which does not interact with the target substance by itself but also a substance which does interact with the target substance. For this reason, in cases where the auxiliary substance interacts with target substances, there is also a problem in that it is difficult to detect a precise interaction between the target substance and the test substance.

In order to solve these problems, for example, JOURNAL OF MOLECULAR RECOGNITION 1999, Vol. 12, pp. 316-321 discloses a method for preparing and immobilizing an IL-2 receptor complex, in which the extracellular domains of IL-2 receptor subunits are integrated with coiled-coil (leucine zipper) domains. This document also discloses that such a complex exhibits a higher affinity than the subunit alone.

However, in this method there is a problem in that expression level of the desired fusion substance is low because a tag allowing a coiled-coil reaction of the receptor needs to be introduced by a recombination technique. In addition, there is also a problem in that coiled-coil reaction sites inhibit the binding activity of the receptor with a test substance, and the versatility of this method is low.

As a technique employing multiple molecules to capture one test substance, a technique called molecular imprinting is disclosed in Japanese Patent Nos. 3527239 and 4036961, and Japanese Patent Application Laid-Open (JP-A) No. 2006-137805. This molecular imprinting is a method for preparing an artificial molecular recognizing substance, in which a target molecule is immobilized on a substrate using an organic polymer, followed by removing the target molecule, whereby a structure corresponding to the molecular shape of the target molecule is left behind as a porous body.

However, in molecular imprinting, since an antibody is immobilized on a substrate by polymerization, an antigen must penetrate into a cross-linked gel matrix structure in order to reach the antibody. Thus it takes time for the antigen to react with the antibody, thereby requiring a highly concentrated antigen in order for a substance to be recognized for certain. Furthermore, the ability to remove the antigen by washing and responsiveness when the antigen is again applied after removal tend to be decreased.

JP-A No. 10-78436 discloses a method for measuring a concentration of an antigen in which either of a VH-region polypeptide or a VL-region polypeptide is immobilized to a solid phase, which utilizes a phenomenon whereby the stability of the Fv region (a recognition site of the antibody) varies depending on the binding with the antibody.

SUMMARY OF INVENTION

When detection is performed in the presence of the target substance, test substance, and auxiliary substance, an immobilization substrate that can precisely detect the interaction between one type of test substance and two or more types of substances with stable binding properties has been demanded. In addition, when immobilization substrates are used for a bioreactor or a biosensor, a production method with greater versatility has been demanded from the viewpoint of production costs.

The present invention has been made in consideration of the above-described circumstances. The present invention provides an immobilization substrate having greater versatility that can precisely detect, with stable binding properties, an interaction between one type of test substance and two or more types of substances.

The present invention includes the following aspects:

<1> An antibody-fragment-immobilizing substrate including a substrate and at least one set of antibody fragments, wherein antibody fragments of each set includes at least two types of separate antibody fragments that are capable of recognizing one type of antigen and that are independently immobilized on the substrate in a positional relationship that allows each of the antibody fragments in one set to bind to the same antigen.

<2> The antibody-fragment-immobilizing substrate according to <1>, wherein the at least two types of antibody fragments includes a VH-region polypeptide and a VL-region polypeptide.

<3> The antibody-fragment-immobilizing substrate according to <1> or <2>, further including a polymer layer and the at least two types of antibody fragments are immobilized on the polymer layer.

<4> The antibody-fragment-immobilizing substrate according to <1>, wherein the thickness of the polymer layer is from 1 nm to 0.5 mm.

<5> The antibody-fragment-immobilizing substrate according to <3> or <4>, wherein the polymer layer is bound to the substrate through a self-assembled monolayer.

<6> The antibody-fragment-immobilizing substrate according to <5>, wherein the thickness of the self-assembled monolayer is from 0.2 nm to 10 µm.

<7> The antibody-fragment-immobilizing substrate according to any one of <1> to <6>, which is used for a bioreactor or biosensor based on a binding reaction between the at least two types of antibody fragments and the antigen.

<8> The antibody-fragment-immobilizing substrate according to any one of <1> to <7>, which is used for a surface plasmon resonance analysis.

<9> A method for producing an antibody-fragment-immobilizing substrate including:

contacting separate antibody fragments of at least two types that are capable of recognizing one type of antigen with the antigen to form a complex whereby each of the antibody fragments binds to the antigen;

immobilizing the complex on a substrate via the antibody fragments in the complex; and removing the antigen from the complex to obtain the antibody-fragment-immobilizing substrate, wherein the antibody fragments are independently immobilized on the substrate in a positional relationship that allows each of the antibody fragments to bind to the same antigen.

<10> The method for producing the antibody-fragment-immobilizing substrate according to <9>, wherein the at least two types of antibody fragments includes a VH-region polypeptide and a VL-region polypeptide.

<11> The method for producing the antibody-fragment-immobilizing substrate according to <9> or <10>, wherein the contacting includes mixing the antibody fragments and the antigen such that the ratio of the number of antigens to the valencies of molecules formed by a combination of antibody fragments is from 0.1:1 to 10:1.

<12> The method for producing the antibody-fragment-immobilizing substrate according to any one of <9> to <11>, wherein the removing is carried out under a condition that reduces the avidity of the antibody fragments and the antigen in the complex.

According to the present invention, an antibody-fragment-immobilizing substrate having greater versatility that can precisely detect an interaction between one type of test substance and two or more types of substances with stable binding properties can be provided.

MODES FOR CARRYING OUT THE INVENTION

Figure 1A:
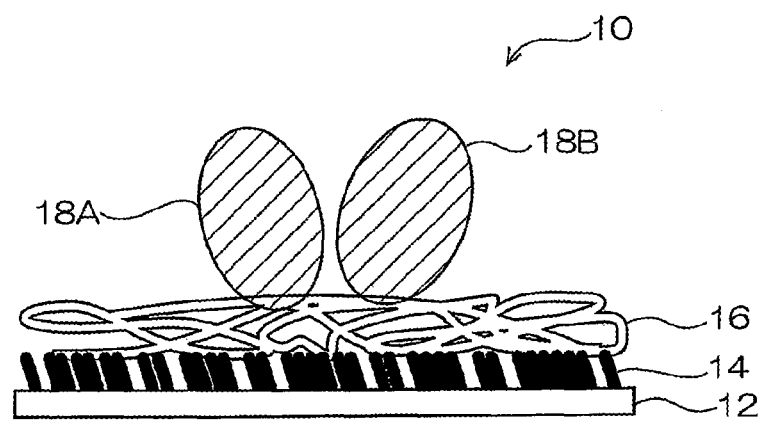
FIG. 1 is a schematic diagram illustrating an example of the immobilization substrate according to the present invention. (A) represents a schematic diagram of the immobilization substrate in the absence of the antigen. (B) represents a schematic diagram of the immobilization substrate in the presence of the antigen.

The immobilization substrate according to the present invention is an antibody-fragment-immobilizing substrate including a substrate and at least one set of antibody fragments, wherein the antibody fragments of each set includes at least two types of separate antibody fragments that are capable of recognizing one type of antigen and that are independently immobilized on the substrate in a positional relationship allowing the each of the antibody fragments in one set to bind to the same antigen.

In an embodiment, the immobilization substrate according to the present invention is an antibody-fragment-immobilizing substrate including a substrate and at least one set of antibody fragments, wherein the antibody fragments of each set includes at least two different and separate antibody fragments that are capable of recognizing one antigen and that are independently immobilized on the substrate in a positional relationship allowing each of the antibody fragments in one set to bind to the same antigen. For example, the present invention provides an immobilization substrate, on which at least two types of separate antibody fragments that are capable of recognizing one type of antigen are independently immobilized on a positional relationship that allows each of the antibody fragments to bind to the antigen.

More specifically, the antibody-fragment-immobilizing substrate may include, for example, a substrate and at least one (for example two or more) antibody-fragment set consisting of two or more different and separate antibody fragments that are capable of recognizing one antigen and that are independently immobilized on the substrate in a positional relationship whereby each of the two or more antibody fragments are capable of binding to the same antigen molecule or anything that forms a single antigen-bearing entity. Therefore, the antibody-fragment-immobilizing substrate of the present invention may include two or more such antibody-fragment sets that may bind to the same antigen-presenting entity or respectively different antigen-presenting entities.

Here, the "separate antibody fragments" represent antibody fragments that are not linked to each other (for example, by disulfide bonds).

In the antibody-fragment-immobilizing substrate of the present invention, since at least two separate antibody fragments that are capable of recognizing one antigen are independently immobilized on the substrate in a positional relationship allowing the at least two separate antibody fragments in one set to bind to the same antigen, the antibody fragments in one set are independent of one another and are placed on the substrate at positions adjacent to one another. Such antibody fragments that cooperatively recognize the antigen can exhibit a higher affinity than the antibody fragments randomly immobilized. In addition, since the each of the antibody fragments are independently immobilized on the substrate in a positional relationship allowing the at least two separate antibody fragments in one set to bind to the same antigen, and since each antibody fragment is bound to the substrate through a part of the antibody, a moiety having the antigen recognition site is allowed to move to such a degree that it can bind to the antigen. Therefore, when the antigen exists, each antibody fragment in one set can easily approach the antigen and can bind to the antigen cooperatively. Accordingly, when the antigen is present as the test substance, the at least two types of separate antibody fragments can bind to the antigen with high affinity and high stability.

In addition, since the antibody fragments are immobilized by using the antigen, at least two types of antibody fragments in one set are immobilized on the substrate at adjacent positions even when each of the antibody fragments has a weak affinity for the antigen. Furthermore, since the antibody fragments are independent of one another, when the affinity between them is low, the antibody fragments do not associate with one another and can easily change their angle independently of one another. Therefore, the immobilization substrate of the present invention can be applied to a catalytic reaction and/or sequential reaction in which flexibility is critical.

The present invention will be further described below.

(I) Immobilization Substrate (1) Substrate

Preferable examples of the substrate of the invention include a substrate in which a functional group is added to any of the following materials: metal oxides such as glass, silica, alumina, titania, zirconia and indium tin oxide (ITO); metal nitrides such as silicon nitride, gallium nitride, aluminum nitride and indium nitride; and synthetic resins, specifically a resin such as Sepharose (tradename), polyethylene, polystyrene, poly(meth)acrylic acid, poly(meth)acrylamide, poly methyl(meth)acrylate, polyethylene terephthalate or polycarbonate or cyclo-olefin polymer. Examples of the functional group include an amino group, a carboxyl group, a maleimide group, an aldehyde group, a succinimide group, a thiol group, a hydrazine group, an isocyanate group, an epoxy group, a vinyl sulfone group, a vinyl group, and a cyano group.

Examples of a method for adding these functional groups include a known method of treating a surface such as plasma treatment, ozone treatment, etching treatment using an acid and/or alkali, or a method using a self-assembled monolayer. From the viewpoint of production suitability, a method using the self-assembled monolayer is preferable.

Examples of a method of forming the self-assembled monolayer include (1-1) a method using a silane coupling agent and (1-2) a method using alkanethiol. Each method will be described below.

(1-1) The Method Using the Silane Coupling Agent

In the method using the silane coupling agent, by providing the silane coupling agent described below to the substrate described above, the self-assembled monolayer can be formed by the silane coupling agent, whereby the functional groups are provided to the substrate.

As the silane coupling agent that can be used in the present invention, a silicon-containing compound represented by the following Formula A-1 may be used to form a covalent bond such as substrate-oxygen-silicon-carbon, thereby providing the functional groups to the substrate surface. In Formula A-1, $X^a$ represents a functional group; $L^a$ represents a linker moiety such as a linear, branched or cyclic carbon chain; $R^a$ represents hydrogen or an alkyl group having 1 to 6 carbon atoms; $Y^a$ represents a hydrolyzable group; m and n each independently represent an integer of from 0 to 3, and the total of m and n is 3.

$$X^a\text{-}L^a\text{-Si}\text{—}(R^a_m)Y^a_n \qquad \text{Formula A-1}$$

Examples of the hydrolyzable group ($Y^a$) include an alkoxy group, a halogen group and an acyloxy group. More specifically, examples of the hydrolyzable group ($Y^a$) include a methoxy group, an ethoxy group and chlorine.

Specific examples of the silane coupling agent include γ-aminopropyl trimethoxysilane, N-β-(aminoethyl)-γ-aminopropyl trimethoxysilane, γ-aminopropyl methyldiethoxysilane, γ-mercaptopropyl trimethoxysilane, and γ-glycidoxypropyltriethoxysilane. Examples of the reaction method of the silane coupling agent include a general method such as a method described in "Effects and usages of silane coupling agents" (Science & Technology Co., Ltd.).

Examples of the functional group ($X^a$) of the silane coupling agent are not limited as long as the functional group ($X^a$) can bind to the below-described polymer and/or complex. Examples thereof include functional groups such as an amino group, a carboxyl group, a hydroxyl group, an aldehyde group, a thiol group, an isocyanate group, an isothiocyanate group, an epoxy group, a cyano group, a hydrazino group, a hydrazide group, a vinyl sulfone group, a vinyl group and a maleimide group. A combination of these functional groups or a derivative thereof may also be used. Among these, functional group ($X^a$) is preferably an amino group or an epoxy group.

(1-2) The Method Using Alkanethiol

In the method using alkanethiol, a metal film is disposed on a surface of the substrate described above, and then the alkanethiol is provided thereon. Here, "disposed on a surface of the substrate" means a case whereby the metal film is disposed on a surface of the substrate such that it directly comes into contact with the substrate, as well as a case whereby the metal film is disposed via another layer without directly coming into contact with a surface of the substrate.

When the metal film is used for a surface plasmon resonance biosensor, a metal for constituting the metal film is not particularly limited, as long as surface plasmon resonance is generated. Preferable examples of the metal include free-electron metals such as gold, silver, copper, aluminum and platinum. Among these, gold is particularly preferable. These metals can be used singly or in combination of two or more kinds thereof. Moreover, in consideration of adherability to the substrate described above, an intermediate layer including chrome or the like may be provided between the substrate and the metal layer.

The film thickness of the metal film is not particularly limited. When the metal film is used for a surface plasmon resonance biosensor, the film thickness is preferably from 0.1 nm to 500 nm, and more preferably from 1 nm to 300 nm. When the film thickness exceeds 500 nm, the surface plasmon phenomena of a medium cannot be sufficiently detected. Moreover, when the intermediate layer including chrome or the like is provided, the thickness of the intermediate layer is preferably from 0.1 nm to 10 nm.

A method of coating a metal film using alkanethiol has been intensively studied by Professor Whitesides at Harvard University, and the details thereof are described in Chemical Review, 105, 1103-1169 (2005), for example. When gold is used as the metal, an alkanethiol represented by the following Formula A-2 (wherein n represents an integer of from 3 to 20, and $X^b$ represents a functional group) may be used as an organic layer-forming compound, whereby a monomolecular film having an orientation can be formed in a self-assemble manner based on an Au—S bond and the van der Waals force between alkyl chains. A self-assembled monolayer may be produced by an extremely easy method, which includes immersion of a gold substrate in a solution of an alkanethiol derivative. More specially, functional groups can be provided to a surface of the substrate, for example, by forming a self-assembled monolayer using a compound in which $X^b$ in Formula A-2 represents an amino group, a carboxyl group, a hydroxyl group, an aldehyde group, a thiol group, an isocyanate group, an isothiocyanate group, an epoxy group, a cyano group, a hydrazino group, a hydrazide group, a vinyl sulfone group, a vinyl group or a maleimide group.

$$HS(CH_2)_nX^b \qquad \text{A-2}$$

In Formula A-2, the number of repetition of an alkylene group, n, is preferably an integer of from 3 to 16, and more preferably an integer of from 4 to 8. The alkylene moiety may be substituted with a multiple bond or a hetero atom such as nitrogen or oxygen. When the alkyl chain of the alkanethiol derivative is too short, formation of the self-assembled monolayer is difficult. When the alkyl chain of the alkanethiol derivative is too long, water solubility is decreased and thus handling thereof is difficult.

A self-assembled monolayer can be formed with a single kind of alkanethiol of Formula A-2, that is, an alkanethiol having one type of the functional group $X^b$. A self-assembled monolayer can also be formed from a mixture of two or more kinds of such alkanethiols.

The film thickness of the self-assembled monolayer is not particularly limited. When the self-assembled monolayer is used for a surface plasmon resonance biosensor, the film thickness is preferably from 0.2 nm to 10 μm, more preferably from 1 nm to 500 nm, and still more preferably from 1 nm to 300 nm. When the film thickness is 10 μm or less, a test substance can easily diffuse in the monolayer. When the film thickness is 0.2 nm or more, the immobilization amount of a substance to be immobilized on the substrate can be increased.

In the invention, the antibody fragments may be directly immobilized to the self-assembled monolayer. However, in order to improve the antigen-binding efficiency of the antibody fragments, it is preferable to form a polymer layer on the self-assembled monolayer so as to provide functional groups for immobilizing the antibody fragments on the substrate surface. The polymer used in the invention is preferably a hydrophilic polymer, and examples thereof include gelatin, agarose, chitosan, dextran, carrageenan, alginic acid, starch, cellulose, or derivatives thereof such as carboxymethyl derivative or water-swellable organic polymers (for example, polyvinyl alcohol, polyacrylic acid, polyacrylamide, polyethylene glycol and derivatives thereof.).

Preferable examples of the hydrophilic polymer that can be used in the invention include a carboxyl group-containing synthetic polymer and a carboxyl group-containing polysaccharide. Examples of the carboxyl group-containing synthetic polymer include polyacrylic acid, polymethacrylic acid and copolymers thereof. Further examples include a methacrylic acid copolymer, an acrylic acid copolymer, an itaconic acid copolymer, a crotonic acid copolymer, a maleic acid copolymer, a partially esterified maleic acid copolymer and a hydroxyl group-containing polymer in which an acid anhydride has been added thereto such as those disclosed, for example, in JP-A No. 59-53836, from line 2, upper right column on page 3, to line 9, lower left column on page 6, and JP-A No. 59-71048, from line 1, lower left column on page 3, to line 3, upper left column on page 5.

Examples of the carboxyl group-containing polysaccharide include any one selected from extracts from natural plants, products obtained by fermentation by microorganisms, synthetic products obtained by enzymes and chemically synthetic products. Specific examples thereof include hyaluronic acid, chondroitin sulfate, heparin, dermatan sulfate, carboxymethyl cellulose, carboxyethyl cellulose, cellouronic acid, carboxymethyl chitin, carboxymethyl dextran, and carboxymethyl starch. As a carboxyl group-containing polysaccharide, a commercially available product can also be used. Specific examples thereof include carboxymethyl dextrans such as CMD, CMD-L and CMD-D40 (trade names, all manufactured by Meito Sangyo Co., Ltd.), sodium carboxymethylcellulose (manufactured by Wako Pure Chemical Industries, Ltd.) and sodium alginate (manufactured by Wako Pure Chemical Industries, Ltd.).

The molecular weight of the hydrophilic polymer used in the invention is not particularly limited. In general, the weight average molecular weight is preferably from $2 \times 10^2$ to $5 \times 10^6$, and more preferably from $1 \times 10^4$ to $2 \times 10^6$. When the weight average molecular weight is less than the above range, the immobilization amount of the antibody fragments on the substrate may be decreased. A weight average molecular weight greater than the above range results in high solution viscosity, thereby making the handling thereof difficult.

The thickness of the polymer layer in an aqueous solution is preferably from 1 nm to 0.5 mm, more preferably from 1 nm to 1 μm, and still more preferably from 100 nm to 500 nm. When the thickness is less than the above range, the immobilized amount of a physiologically active substance becomes small, which makes interaction of the physiologically active substance with a test substance less likely to occur.

When the film thickness exceeds the above range, the uniformity of the polymer layer may not be maintained, and a test substance may be inhibited from diffusing into the polymer film. In particular, when the interaction is detected from the side of a sensor substrate opposite to a hydrophilic polymer-immobilized surface thereof, the detection sensitivity may be decreased due to the long distance from the detection surface to an interaction-forming part.

The thickness of the hydrophilic polymer in an aqueous solution can be evaluated by, for example, AFM or ellipsometry.

When the carboxyl group-containing polymer is used, the complex can be immobilized on the substrate via functional groups provided to the substrate surface by activating carboxyl groups of the polymer. Examples of the method for activating the carboxyl group-containing polymer include a known method, for example, a method in which a carboxyl group-containing polymer is activated by using a water-soluble carbodiimide such as 1-(3-dimethylaminopropyl)-3-ethylcarbodiimide (EDC) and N-hydroxysuccinimide (NHS), and a method in which a carboxyl group-containing polymer is activated by using EDC alone. The polymer having the carboxyl group activated by using these methods can be reacted with the substance having an amino group to attach the hydrophilic polymer to the substrate.

Examples of the method for activating the carboxyl group-containing polymer also include a method using a nitrogen-containing compound. Specific examples of the nitrogen-containing compound include a compound represented by the following Formula (Ia) or Formula (Ib) (wherein, $R^1$ and $R^2$ each independently represent an unsubstituted or substituted carbonyl group, a carbon atom which may have a substituent, or a nitrogen atom which may have a substituent; $R^1$ and $R^2$ may be linked to each other to form a 5- or 6-membered ring; A represents a carbon atom having a substituent, or a phosphorus atom having a substituent; M represents an element which forms an (n−1)-valent counter ion as a whole; and X represents a halogen atom).

(Ia)

(Ib)

In Formulae (Ia) and (Ib), $R^1$ and $R^2$ each independently represent an unsubstituted or substituted carbonyl group, a carbon atom which may have a substituent, or a nitrogen atom which may have a substituent, and preferably $R^1$ and $R^2$ are linked to each other to form a 5- or 6-membered ring. Preferable examples of the nitrogen-containing compound include hydroxysuccinimide, hydroxyphthalimide, 1-hydroxybenzotriazole, 3,4-dihydroxy-3-hydroxy-4-oxo-1,2,3-benzotriazine, and derivatives thereof.

Preferable examples of the nitrogen-containing compound also include the following compounds (Ic), (Id) and (Ie).

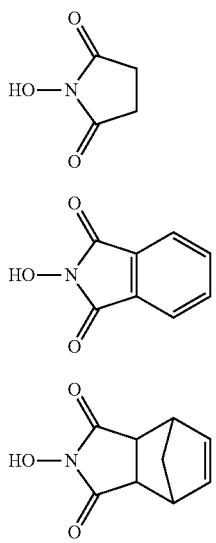

Preferable examples of the nitrogen-containing compound include a compound represented by the following Formula (II) (wherein, Y and Z each independently represent CH or a nitrogen atom).

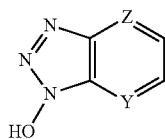

Preferable examples of the compound represented by Formula (II) include the following compounds (II-1) to (II-3).

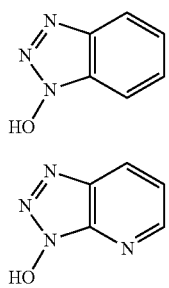

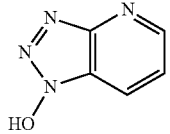

Preferable examples of the nitrogen-containing compound also include a compound represented by the following Formula (II-4).

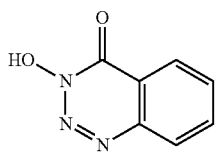

Preferable examples of the nitrogen-containing compound further include a compound represented by the following Formula (III) (wherein A represents a carbon atom having a substituent, or a phosphorus atom having a substituent; Y and Z each independently represent CH or a nitrogen atom; M represents an element which forms an (n−1)-valent counter ion as a whole; and X represents a halogen atom).

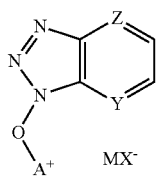

In Formula (III), the substituent which the carbon atom or phosphorus atom represented by A has is preferably an amino group having a substituent. More specifically, a dialkylamino group such as a dimethylamino group or a pyrrolidino group is preferable. Examples of the element represented by M include a phosphorus atom, a boron atom and an arsenic atom. Among these, a phosphorus atom is preferable. Examples of the halogen atom represented by X include a fluorine atom, a chlorine atom, a bromine atom and an iodine atom. Among these, a fluorine atom is preferable.

Specific examples of the nitrogen-containing compound represented by Formula (III) include the following compounds (III-1) to (III-6).

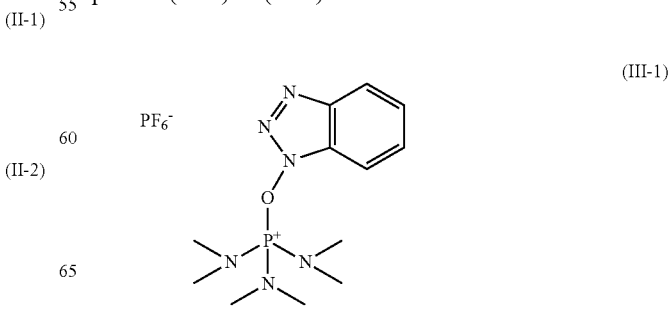

-continued (III-2) 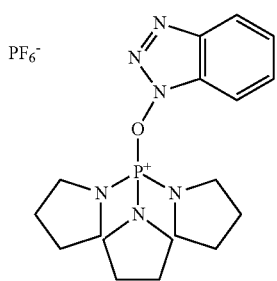

(III-3) 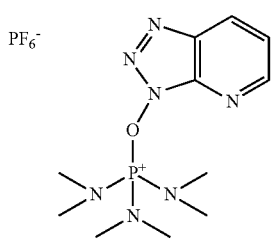

(III-4) 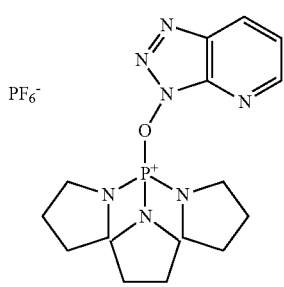

(III-5) 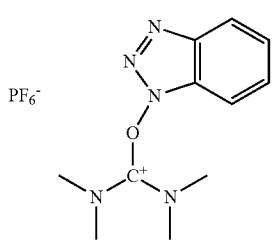

(III-6) 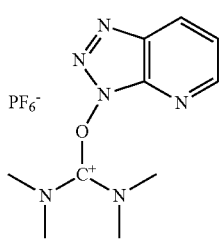

Preferable examples of the nitrogen-containing compound further include a compound represented by the following Formula (IV) (wherein A represents a carbon atom having a substituent, or a phosphorus atom having a substituent; M represents an element which forms an (n−1)-valent counter ion as a whole; and X represents a halogen atom).

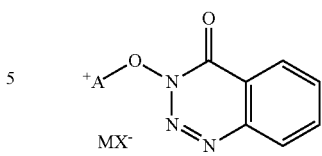
(IV)

Preferable examples of the nitrogen-containing compound represented by Formula (IV) include the following compound (IV-1).

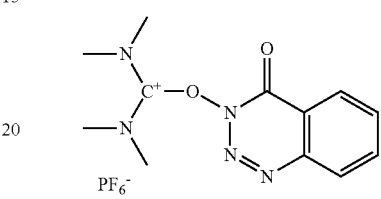
(IV-1)

Examples of the method for activating the carboxyl group-containing polymer also include a method using a phenol derivative having an electron-withdrawing group. The σ value of the electron-withdrawing group is preferably 0.3 or more. Specific examples of the phenol derivative having an electron-withdrawing group include the following compounds (V-1) to (V-4).

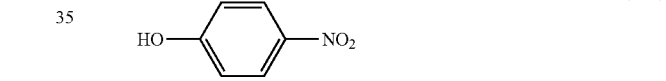
(V-1)

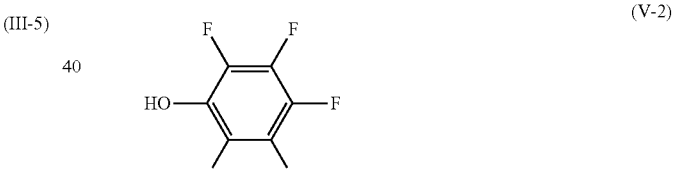
(V-2)

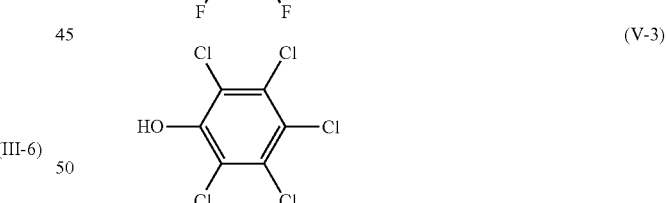
(V-3)

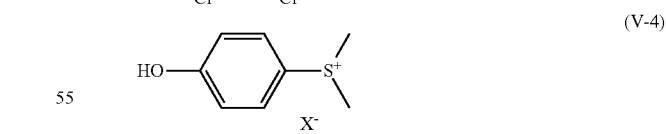
(V-4)

Any of the above-described carbodiimide derivative, nitrogen-containing compound and phenol derivative may be used singly, or in combination of two or more kinds thereof, if desired. It is preferable to use the carbodiimide derivative and the nitrogen-containing compound in combination.

Examples of the method for activating the carboxyl group-containing polymer further include a method using the following compound (V-6). The compound (V-6) may be used singly, or in combination with the carbodiimide derivative, the nitrogen-containing compound and/or the phenol derivative.

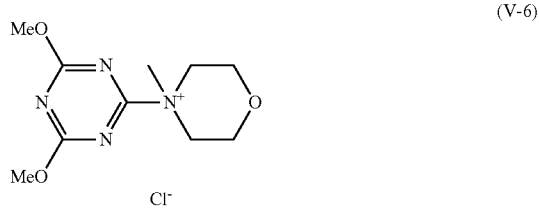 [SMILES: COc1nc(OC)nc([N+]2(C)CCOCC2)n1 ; [Cl-]]

(V-6)

In addition, preferable examples of the method for activating the carboxyl group of the carboxyl group-containing polymer include methods such as that described in paragraph Nos. [0011] to [0022] of JP-A No. 2006-58071 (i.e., a method of forming a carboxylic acid amide group by activating the carboxyl group on a surface of a substrate with a compound selected from a uronium salt having a particular structure, a phosphonium salt having a particular structure or a triazine derivative having a particular structure); and methods such as that described in paragraph Nos. [0011] to [0019] of JP-A No. 2006-90781 (i.e., a method of forming a carboxylic acid amide group by activating the carboxyl group on a surface of a substrate with a carbodiimide derivative or a salt thereof, converting the activated group to an ester group using a nitrogen-containing heteroaromatic compound having a hydroxyl group, a phenol derivative having an electron-withdrawing group or an aromatic compound having a thiol group, and then reacting the resulting ester group with an amine).

The polymer containing an activated carboxyl group may be prepared as a polymer solution and reacted with the substrate. Alternatively, the polymer containing an activated carboxyl group of the present invention may be formed in a thin film on the substrate by using a method such as a spin coating method, and reacted with the substrate in the thin film state. The polymer is preferably reacted in the thin film state with the substrate.

As described above, the polymer of the invention is preferably reacted in the thin film state with the substrate. As a method for forming a thin film on the substrate, known methods can be used. Specific examples of such methods that can be used include an extrusion coating method, a curtain coating method, a casting method, a screen printing method, a spin coating method, a spray coating method, a slide bead coating method, a slit and spin method, a slit coating method, a die coating method, a dip coating method, a knife coating method, a blade coating method, a flow coating method, a roll coating method, a wire-bar coating method, and a transfer printing method. These methods are described in, for example, "Progress in Coating Technology (*Coating Gijutsu no Shinpo*)" written by Yuji Harazaki, Sogo Gijyutsu Center (1988); "Coating Technology (*Coating Gijutsu*)" Technical Information Institute Co., Ltd. (1999); "Aqueous Coating Technology (*Suisei Coating no Gijutsu*)" CMC (2001); "Evolving Organic Thin Film: Edition for Deposition (*Shinka-suru Yuuki Hakumaku: Seimaku hen*)" Sumibe Techno Research Co., Ltd. (2004); and "Polymer Surface Processing Technology (*Polymer Hyomen Kako Gaku*)" written by Akira Iwamori, Gihodo Shuppan Co., Ltd. (2005). In the present invention, the method for forming a thin film on the substrate is preferably a spray coating method or a spin coating method, and more preferably a spin coating method, since a coating film having a controlled film thickness can be readily produced by such a method.

(2) Antibody Fragment

In the present invention, at least two types of antibody fragments capable of recognizing one type of antigen are immobilized on the above-described substrate.

Here, two or more types of antibody fragments capable of recognizing one type of antigen may be immobilized on the substrate, or plural types of antibody-fragment sets each consisting of such antibody fragments may be immobilized on the substrate. By using the plural types of antibody-fragment sets, plural types of antigens can be recognized with one immobilization substrate.

The type of the antigen is not specifically restricted as long as it can interact with an antibody, and can be appropriately selected depending on the target substance to be detected. Further, the antibody fragment can be appropriately selected as an antibody capable of interacting with such an antigen.

Any antibodies can be used as long as antibody fragments of two or more types can individually or cooperatively recognize and bind to one antigen. Examples of such plural antibody fragments include two or more types of antibody fragments each having at least a part of an antigen recognition site for (the same) one epitope on one type of antigen, two or more types of antibody fragments each having an antigen recognition site for a different epitope on one type of antigen, and antibody fragments each having any one of plural hypervariable regions for one epitope. Such plural antibody fragments can also be used in combination, as long as the antibodies recognize one antigen.

Preferable examples of the antibody fragment of the invention include a VH-region polypeptide and VL-region polypeptide, from the viewpoint of an antigen binding ability.

The length of VH-region polypeptide and VL-region polypeptide may be either longer or shorter than the VH region and VL region of the antibody, respectively, as long as they can bind to a target antigen in association with each other. These polypeptides can be produced from a monoclonal antibody made by a hybridoma technique by using a conventional method. For example, the polypeptides can be obtained as follows.

First, a monoclonal antibody capable of recognizing a desired test substance is produced by a known method. The gene encoding the variable region of this antibody is then specified by a method using a cDNA library and hybridization technique, followed by cloning this gene into a vector. The sequence encoding the VH and/or VL region is then obtained from this recombinant vector, and this sequence fragment is subcloned into an expression vector. By expressing this gene in host cells, the required amount of VH and/or VL can be obtained.

In order to obtain the VH/VL coding sequence from the antibody gene, the desired sequence region may be isolated by cleavage with a restriction enzyme to be amplified in a cloning vector, or the desired sequence may be amplified by PCR. When VH and/or VL are/is expressed in host cells, a gene encoding any reporter molecule may also be cloned into the expression vector and VH and/or VL can be expressed as a fusion protein or a chimera protein with the reporter molecule.

In addition to the above methods, VH and/or VL can be obtained by proteolysis of the antibody molecule using a protease. This method has an advantage of saving time and effort on the gene cloning.

The VH-region polypeptide and the VL-region polypeptide may be a fusion product with a biomolecule. Such a fusion product has an advantage of improving the stability.

The biomolecule which can be fused with the VH-region polypeptide or the VL-region polypeptide is not particularly restricted, and examples thereof include alkaline phosphatase, protein G, eGFP, eYFP, β-galactosidase, GST, chitin binding protein (CBP), NusA, thioredoxin, DsbA, DsbC, and maltose binding protein (MBP). Among these, in order to further increase stability, MBP is preferably used.

These fusion products can be produced by a conventional method. For example, the fusion product can be obtained by incorporating the gene encoding the biomolecule into a vector at the time of the above-described gene cloning so as to be expressed simultaneously, or by adding a linker to the VH-region polypeptide or the VL-region polypeptide to fuse with the biomolecule. The method for producing the fusion product can be appropriately selected depending on the type and size of the biomolecule to be fused.

An antibody fragment other than the VL-region polypeptide and the VH-region polypeptide can be produced in a manner similar to the method for producing the VL-region polypeptide and the VH-region polypeptide. Such a method is easily applicable by those skilled in the art.

(3) A Method for Producing the Antibody-Fragment-Immobilizing Substrate

A method for producing the antibody-fragment-immobilizing substrate according to the present invention includes:

contacting separate antibody fragments of at least two types that are capable of recognizing one type of antigen with the antigen to form a complex whereby each of the antibody fragments binds to the antigen;

immobilizing the complex on a substrate via the antibody fragments in the complex; and removing the antigen from the complex to obtain the antibody-fragment-immobilizing substrate, wherein the antibody fragments are independently immobilized on the substrate in a positional relationship that allows each of the antibody fragments to bind to the same antigen.

According to the production method of the invention, since the complex composed of the antibody fragments of at least two types and the antigen is immobilized on the substrate, and then the antigen is removed from the complex, the antibody-fragment-immobilizing substrate, in which the antibody fragments are independently immobilized on the substrate in a positional relationship that allows each of the antibody fragments to bind to the same antigen in the presence of the antigen, can be easily produced.

According to the production method of the invention, an antibody-fragment-immobilizing substrate including a substrate and at least one set of (for example two or more sets of) antibody fragments may be obtained, in which the antibody fragments of each set include the at least two types of separate antibody fragments that have been immobilized on the substrate as described above.

When forming the complex, the complex composed of the antibody fragments and the antigen can be formed by a known technique. More specifically, the complex is easily obtained by mixing the above-described antibody fragments and antigen.

The mixing ratio of two or more types of antibody fragments to the antigen can be appropriately set depending on a binding mode of an antibody toward an antigen. In consideration of efficiency and in order to prevent excess immobilization of the antigens, the ratio of the number of antigens to the valencies of molecules formed by a combination of antibody fragments is from 0.1:1 to 10:1.

The mixing ratio of the antibody fragments and the antigen can be appropriately adjusted depending on affinity of the antibody fragments for an antigen, immobilization efficiency of the antigen per se to the substrate directly, or the like. In general, when the antigen is expected to have a sufficient affinity for the antibody fragments, the ratio of the number of antigens to the valencies of molecules formed by a combination of antibody fragments is from 0.1:1 to 1:1, and more preferably from 0.1:1 to 0.3:1. On the other hand, when the antigen is expected to have a low affinity or expected to be difficult to immobilize on the substrate directly, for example, when a low molecular compound or the like is used as the antigen, it is preferable to use an increased amount of the antigen. More specifically, the ratio of the number of antigens to the valencies of molecules formed by a combination of antibody fragments is preferably from 0.5:1 to 1.5:1.

Here, "the valencies of molecules formed by a combination of antibody fragments" means the number of the antigen-binding sites present in the molecules formed by a combination of antibody fragments. That is, when a molecule formed by a combination of antibody fragments constitutes a complete antibody molecule, the valencies of the molecules are equal to that of the antibody molecules. When a molecule formed by a combination of antibody fragments does not constitute a complete antibody molecule, the valency thereof is considered to be 1 as long as one antigen-binding site is included therein.

The antigen may be a low molecular weight molecule, or a high molecular weight molecule such as a protein. Although the complex may be formed by any number of molecules, in order to facilitate the control of the quantitative ratio, the number of molecules forming the complex is preferably three molecules such as two types of the antibody fragments and one antigen.

For example, when an anti-lysozyme VH-region polypeptide, an anti-lysozyme VL-region polypeptide and a lysozyme are used, since the VH-region polypeptide and the VL-region polypeptide each interact with the antigen in a ratio of 1:1, a molecule formed by the combination of the VH-region polypeptide and the VL-region polypeptide has a valency of 1. Therefore, the complex can be readily obtained by mixing the VH-region polypeptide, VL-region polypeptide, and antigen in an equal number ratio in an aqueous solution, that is, in a ratio of 1:1:1. In order to prevent decreasing of binding efficiency to the antibody fragments caused by the direct immobilization of lysozyme on the substrate, the number ratio of the antigen is preferably less compared with the valency of the antibody fragment. The mixing ratio among the VH-region polypeptide, VL-region polypeptide, and antigen is preferably from 10:10:1 to 10:10:9, and more preferably from 10:10:1 to 10:10:3.

When immobilizing the complex, the complex formed by the procedure described above is linked to the substrate by conducting the reaction appropriately in accordance with the type of functional group provided to the substrate. In this case, since the antigen-recognition site of the antibody fragment is protected by binding of the antigen, no additional protective treatment is required. Methods for linking the complex to the substrate are well known by those skilled in the art. Examples thereof include a method of activating a carboxyl group using EDC described above or the like and linking to a complex via an amino group, or a method in which a complex is linked to the substrate by a reaction of a maleimide group with a thiol group, but the present invention is not restricted thereto.

When the immobilization substrate according to the present invention is used in a biosensor utilizing surface plasmon resonance, the immobilization amount (density) of the complex bound to the immobilization substrate is preferably from 10 pg/mm$^2$ to 20,000 pg/mm$^2$, more preferably from 200 pg/mm$^2$ to 10,000 pg/mm$^2$, and still more preferably from 500 pg/mm$^2$ to 8,000 pg/mm$^2$. The density can be determined by the following method. When the density is determined by an actual measurement, the complex is linked to a substrate, and then the weight of the biological molecule bound to the substrate is determined with a QCM measurement technique or a SPR measurement technique. Furthermore, the immobilization amount of each molecule can be determined by labeling each molecule with a fluorescence molecule.

When removing the antigen from the complex, the complex is immobilized on the substrate and then the antigen is removed. Since each of the antibody fragments is independently immobilized on the substrate, the antigen can be readily removed. Therefore, when the substrate is used as the immobilization substrate, binding reproducibility of the antigen may not decrease.

The removal of the antigen is readily carried out by using an appropriate washing solution. Any solution can be used as the washing solution as long as it reduces the avidity of the antigen and the antibodies in the complex. Examples of a condition for reducing the avidity include altering a pH toward an acidic side or an alkali side, and/or increasing a salt concentration. The washing solution varies depending on the type of the antibody fragment and antigen or the like, and examples thereof include an acidic glycine buffer with which the pH may be adjusted to 2 or less; an alkaline NaOH solution with which the pH may be adjusted to 10 or more; and a borate buffer with which the salt concentration may be adjusted to 0.5 M or more.

In addition, an acidic buffer containing arginine, a buffer containing guanidine or a buffer containing urea can be appropriately used.

Here, the condition of the washing treatment with the washing solution can be appropriately adjusted. In order not to impair the activity of the antibody fragment, the time for the washing treatment is in general 10 minutes or less, and preferably one minute or less. From the viewpoint of reproducibility, the time for the washing treatment is preferably 5 seconds or more.

In this manner, the antibody-fragment-immobilizing substrate can be obtained, wherein the antibody fragments are independently immobilized on the substrate in a positional relationship that allows each of the antibody fragments in one set to bind to the same antigen. In this antibody-fragment-immobilizing substrate, the antibody fragments independently immobilized on the substrate have a degree of freedom and are in a state such that the antibody can bind to the antigen. Therefore, when the antigen approaches the antibody fragments to be bound, the antibody fragments approach one another to bind to the antigen. Such antibody fragments exhibit a higher affinity compared with when each of the antibody fragments binds to the antigen individually. According to this method, the antibody-fragment-immobilizing substrate with such a high affinity can be easily obtained.

Figure 1B:
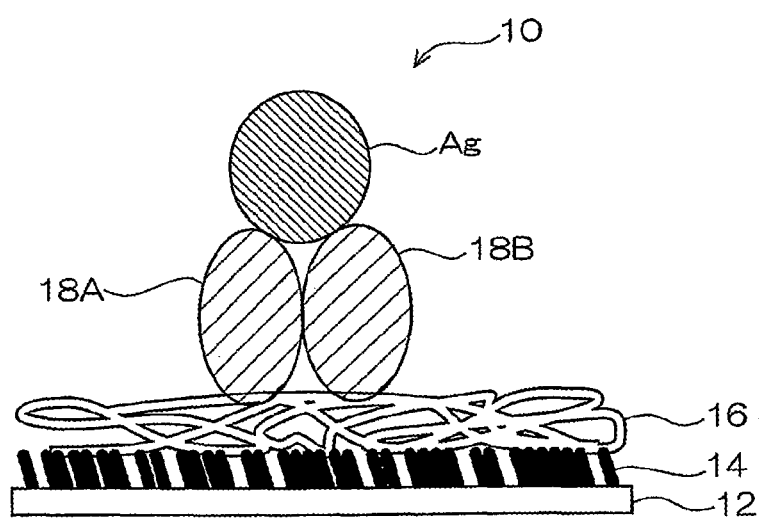
Figure 2:
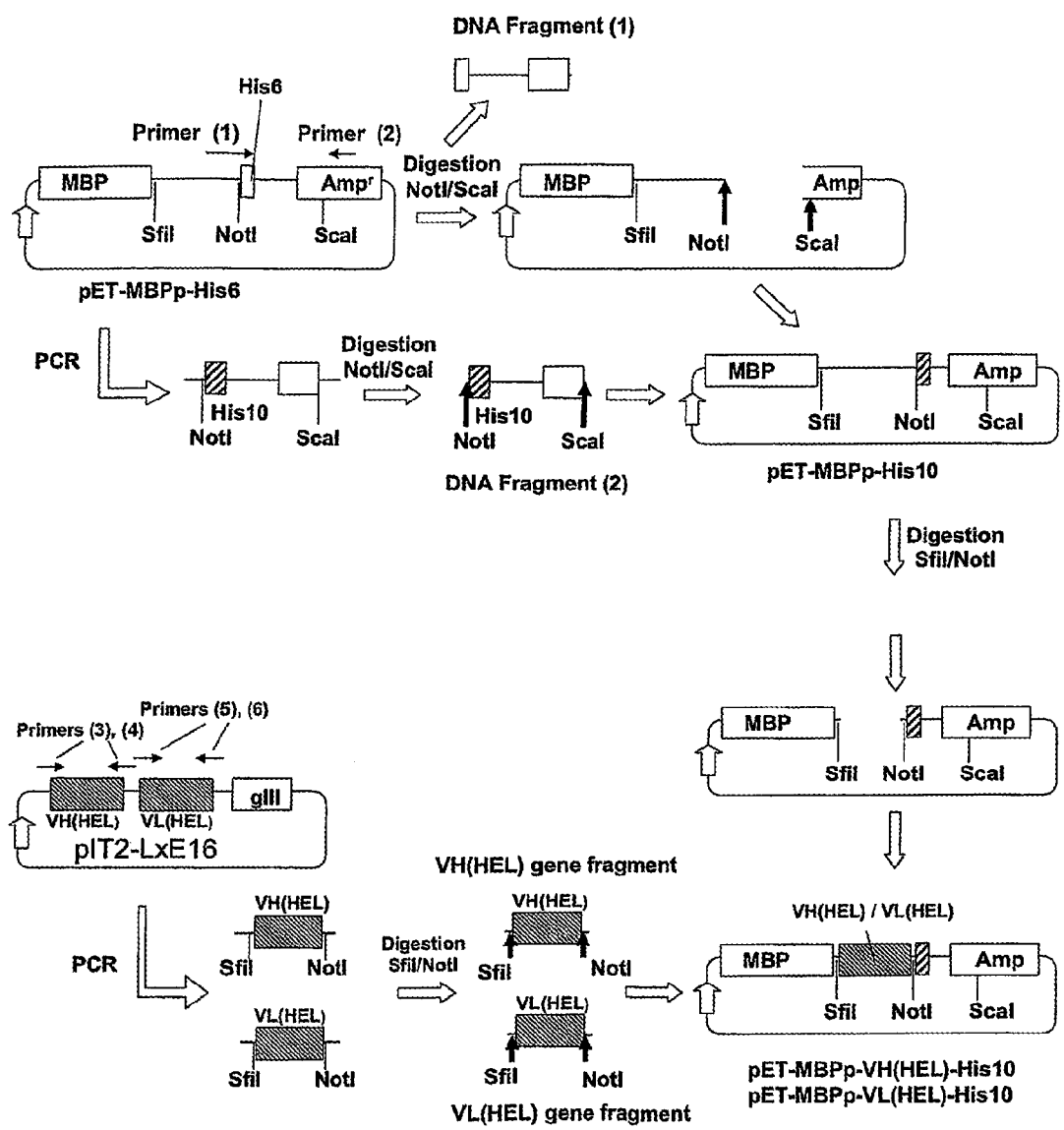
FIG. 2 is a scheme for preparing the expression vectors according to Examples described in the present invention.

For example, FIGS. 1A and 1B show an immobilization substrate 10, which is an example of the antibody-fragment-immobilizing substrate according to the present invention. In the immobilization substrate 10, antibody fragments 18A and 18B are immobilized on a substrate 12 through a self-assembled monolayer 14 and a polymer layer 16. The antibody fragment 18A and the antibody fragment 18B are bound to the substrate 12 through one end of each antibody fragment such that the other end of each antibody fragment can move freely, and are independently immobilized on the substrate 12 in a positional relationship that allows the antibodies to cooperatively bind to an antigen Ag if present (see FIG. 1A).

When the antigen Ag approaches the immobilization substrate 10, the antibody fragments 18A and 18B recognize and bind to the antigen Ag. When binding, the antibody fragments 18A and 18B approach each other centering around the antigen Ag, and bind to Ag, whereby the antibodies can bind to the antigen with a higher affinity than when the respective antibodies bind to the antigen independently (see FIG. 1B).

As described above, by immobilizing the complex formed by two or more antibody fragments and one or more antigens on the substrate through the two or more antibody fragments and then removing only the antigens, the antibody-fragment-immobilizing substrate which can be utilized in an immunoassay using an antigen-antibody reaction can be obtained.

According to the present invention, regardless of the degree of the affinity for the antigen, the target antibody fragments can be immobilized on the substrate in a relative position adjacent to one another that allows each of the antibodies to bind to the same antigen.

In addition, even when a small number of epitopes for the antibody is available, for example, when the antigen is a low molecule, since the antibody fragments are immobilized on the substrate in an adjacent position capable of binding to the antigen cooperatively, the antibody-fragment-immobilizing substrate of the present invention has a high antigen-binding ratio. While it depends on the amount of the antibody fragments of two or more types that are immobilized on the substrate and the type of the antigen used, for example, when the amount of the antibody fragment immobilized is 0.025 pmol/mm$^2$, "high antigen-binding ratio" preferably means an antigen-binding ratio of 1% or more, more preferably an antigen-binding ratio of 6% or more, and still more preferably an antigen-binding ratio of 10% or more, with respect to a calculated ideal antigen-binding amount for the immobilizing amount. The term "ideal antigen-binding amount" used herein refers to a binding amount of antigen calculated on the assumption that each of the antibody fragments are immobilized in equimolar amounts and have a 100% activity. The antigen-binding ratio is obtained by dividing the binding amount of the antigen by the ideal antigen-binding amount. More specifically, the antigen-binding ratio in the present invention is obtained by measuring the immobilization amount of the antibody fragments and the binding amount of the antigen when the antigen is added by a SPR measurement technique and calculating the ratio based on the above-described assumption.

(II) Application of the Immobilization Substrate According to the Present Invention The immobilization substrate according to the present invention can be applied to a biosensor or a bioreactor based on a binding reactivity between the antibody fragment and the antigen (for example, see "Bioreactor Technique", 1988, CMC Publishing Co., Ltd., and "Biochip and Biosensor", 2006, Kyoritsu Shuppan Co., Ltd.). Here, the bioreactor refers to a reactor applied for production of useful materials, generation of energy, degradation of environmental pollutants or the like by utilizing a biochemical reaction by biological catalysts such as enzymes, bacteria cells, cells, or organelles. Here, the biosensor term means is intended to be interpreted most broadly, and means a sensor that measures and/or detects a target substance by converting an interaction between biological molecules into a signal such as an electrical signal. Hereinafter, the application to the bioreactor and the biosensor will be described.

(1) Application to the Bioreactor

A bioreactor capable of carrying out generation of useful substances, reaction, or the like using an insoluble substrate immobilizing an enzyme is described (for example, Examined utility model application publication (JP-Y) Nos. 4-18398 and 4-18399). The substrate according to the present invention, for example, in the form of a substrate having a support (for example, a porous material such as ceramic or polysulfone), a polymer membrane bound to this substrate surface, and an enzyme and an auxiliary substance for an enzyme activity which are bound to this polymer membrane can be applied, as such insoluble substrate, to the bioreactor.

(2) Application to a Biosensor

In general, a biosensor is composed of a receptor portion recognizing target chemicals to be detected and a transducer portion converting a physical change or a chemical charge generated at the receptor portion into an electric signal. Examples of a combination of substances having a mutual affinity in a living body include a combination of enzyme and substrate, a combination of enzyme and coenzyme, a combination of antigen and antibody, and a combination of hormone and receptor. The biosensor employs a principle that, by immobilizing one of the substances with mutual affinities of such a combination on a substrate and using it as a molecule-recognizing substance, the corresponding other substance is selectively measured. The substrate according to the present invention can be applied to be, for example, a substrate having a support (for example, a porous material such as ceramic or polysulfone), a polymer membrane bound to this substrate surface, and an enzyme and an auxiliary substance for an enzyme activity which are bound to this polymer membrane, to further improve specificity compared with conventional biosensor.

For example, a surface plasmon resonance biosensor is composed of a member containing a portion for transmitting and reflecting a light radiated from the sensor and a portion for immobilizing a bioactive substance. The immobilization substrate according to the invention can be used as a member capable of immobilizing the same kind of substance (an antigen) as the substance that has been removed by washing in advance.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light.

Example of a surface plasmon measurement device for analyzing the properties of a substance to be measured using a phenomenon in which a surface plasmon is excited by a lightwave include a device using a system known as the Kretschmann configuration (for example, JP-A No. 6-167443). The surface plasmon measurement device using the above system basically includes a dielectric block formed in a prism-like shape, a metal film formed on a face of the dielectric block to contact with a substance to be measured such as a sample solution, a light source for generating a light beam, an optical system for allowing the light beam to enter the dielectric block at various angles so that total reflection conditions can be obtained at the interface between the dielectric block and the metal film, and a light-detecting means for detecting the state of surface plasmon resonance, that is, the state of attenuated total reflection, by measuring the intensity of the light beam totally reflected at the interface.

In addition, examples of a similar measuring device utilizing attenuated total reflection (ATR) include a leaking mode measurement device such as those described in "*Bunko Kenkyu*" (Journal of the Spectroscopical Society of Japan) Volume 47, Issue 1 (1998), pages 21-23 and 26-27. This leaking mode measurement device basically includes, for example, a dielectric block formed in a prism-like shape, a cladding layer formed on a surface of the dielectric block, an optical waveguiding layer that is formed on the cladding layer and that will be brought into contact with a sample solution, a light source for generating a light beam, an optical system for allowing the light beam to enter the dielectric block at various angles so that total reflection conditions can be obtained at the interface between the dielectric block and the cladding layer, and a light-detecting means for detecting the excited state of the guide mode, that is, the state of attenuated total reflection, by measuring the intensity of the light beam totally reflected at the interface.

Examples of the constitution of the biosensor of this system are described, for example, in examined Japanese patent publication (JP-B) No. 6-27703, from line 48 on page 4 to line 15 on page 14, and FIGS. 1 to 8, and U.S. Pat. No. 6,829,073, from line 31 of column 6 to line 47 of column 7, and FIGS. 9A and 9B.

For example, one embodiment of the present invention includes a structure in which a thin layer forming a planer waveguiding layer is provided on a base material (for example, PYREX (registered trademark) glass). A so-called waveguide body consists of a waveguiding layer and a base material. The waveguiding layer may have a multi-layered structure including, for example, an oxide layer ($SiO_2$, $SnO_2$, $Ta_2O_5$, $TiO_2$, $TiO_2$—$SiO_2$, $HfO_2$, $ZrO_2$, $Al_2O_3$, $Si_3N_4$, HfON, SiON, scandium oxide, or a mixture thereof) or a plastic layer (for example, polystyrene, polyethylene or polycarbonate). In order for a light beam to travel through the waveguiding layer by total internal reflection, it is necessary that the refractive index of the waveguiding layer be higher than that of the index of adjacent media (for example, the base material or an additional layer described below). A diffraction grating is arranged on or in the base material, on the waveguiding layer surface facing the substance to be measured, or in the volume of the waveguiding layer. The diffraction grating can be formed on or in the base material by an embossing technique, a holographic technique or other methods. Subsequently, the thin waveguiding layer having a higher refractive index is provided to cover the upper surface of the diffraction grating. The diffraction grating has functions of converging an incident light to the waveguiding layer, allowing a guided mode to leave the waveguiding layer, or partly transmitting the mode toward the direction of travel and partly reflecting a guided mode. The grating region of the waveguiding layer is covered with the additional layer. The additional layer may be a multilayer, as necessary. The additional layer may be imparted with a function of selective detection of a specific substance in a sample to be measured. In a preferable aspect of the invention, a layer having the detection function can be disposed at the outermost surface of the additional layer. As the layer having the detection function, a layer that can immobilize a bioactive substance thereon can be used.

Another embodiment of the present invention includes a waveguide in which an arrayed waveguide grating is incorporated into a well of a micro plate (Japanese National Phase Publication No. 2007-501432). This arrayed waveguide grating on the bottom of microplate wells enables the high-throughput screening for drugs or chemicals.

In order to detect a bioactive substance on the upper layer (detection region) of the diffraction grating waveguide, a change of refraction properties is detected by detecting an incident light and reflected light. For this purpose, one or more light sources (for example, a laser or a diode) and one or more detectors (for example, a spectrometer, a CCD camera or other photodetector) can be used. Examples of a method for measuring a refractive index change include two different operational modes—a spectroscopic method and an angle method. In the spectroscopic method, a broad band beam is sent, as the incident light, to the diffraction grating waveguide and reflected light is collected to be measured, for example, with a spectrometer. By observing the spectrum position of a resonance wavelength (peak), a change of the refractive index on or near the surface of the diffraction grating waveguide, that is, binding of the bioactive substance, can be measured. In the angle method, a light with a nominal single wavelength is focused to give an irradiation angle within a certain range, and is forwarded into the diffraction grating waveguide. A reflected light is measured with a CCD camera or other photodetector. By measuring a position of a resonance angle reflected by the diffraction grating waveguide, a change of the refractive index on or near the surface of diffraction grating waveguide, that is, binding of the bioactive substance, can be measured.

Hereinafter, the immobilization substrate of the invention will be described in more detail with reference to examples, but the invention is not limited to the examples. Further, "parts" and "%" indicate quantities in terms of mass, unless otherwise specified.

EXAMPLES

Example 1

(1) Preparation of Anti-Lysozyme VH-Region Polypeptide and Anti-Lysozyme VL-Region Polypeptide Abbreviations used in the Examples are as follow:
LB: culture medium containing 1% BACTO (Registered tradename) Tryptone, 0.5% Yeast Extract and 0.5% NaCl
LBA: LB containing 100 μg/ml of ampicillin
LBAG: LB containing 100 μg/ml of ampicillin and 0.1% glucose
LBAG plate: LB agar medium containing 100 μg/ml of ampicillin and 0.1% glucose
SOC: culture medium containing 2% BACTO (Registered tradename) Tryptone, 0.5% Yeast Extract, 0.05% NaCl, 2.5 mM KCl, 20 mM glucose and 10 mM MgCl$_2$
TAE buffer: 40 mM Tris-acetate buffer (pH 8.3) containing 1 mM EDTA
TALON Buffer: 50 mM sodium phosphate buffer (pH 7.0) containing 300 mM NaCl
TALON Elution Buffer: TALON Buffer (pH 7.0) containing 500 mM imidazole
IPTG: isopropyl-β-thiogalactopyranoside
HBS-N buffer: 10 mM HEPES, 150 mM NaCl, pH 7.4

In all experiments, water purified with MILLI-Q (trade name, manufactured by Millipore Co., Billerica, Mass., USA) was used. Hereinafter, this purified water is referred to as milliQ water. Unless otherwise specified, general reagents used were obtained from Sigma-Aldrich Co. (St. Louis, Mo., USA), Nacalai Tesque (Kyoto, Japan), Wako Pure Chemical Industries, Ltd. (Osaka, Japan), or Kanto Chemical Co. Inc. (Tokyo, Japan). Oligo DNAs were synthesized by Texas Genomics Japan (Tokyo, Japan) or Invitrogen (Tokyo, Japan).

The genotypes of *E. coli* XL10-Gold and OverExpress C41 are shown in Table 1, and the primer sequences used for PCR are shown in Table 2.

TABLE 1

<*E. coli.*>

XL10-Gold:
Tetr Δ(mcrA) 183 Δ(mcrCB-hsdSMR-mrr) 173 endA1 supE44 thi-1 recA1 gyrA96 relA1 lac Hte [F′proAB lacIqZΔM15 Tn10 (Tet$^r$) Amy Cam$^r$]
OverExpress C41(DE3):
F$^-$, ompT, hsdS$_B$(r$_B^-$ m$_B^-$), gal(λcI 857, ind1, Sam7, nin5, lacUV5-T7gene1), dcm(DE3)

TABLE 2

<Primer>

(1) SEQ ID NO: 1
AAAAAAAGCGGCCGCGGAGCATCATCACCATCACCACCACCACCACCACT GAGATCCGG
(The underline indicates the NotI site and the double-underline indicates the His10 sequence.)

(2) SEQ ID NO: 2
CCAATGCTTAATCAGTGA (3) SEQ ID NO: 3
CTTTCTATGCGGCCCAGCCGGCCATGGCCGAKGTSVAGCTTCAGGAGTC
(The underline indicates the SfiI site.)

(4) SEQ ID NO: 4
AAAAAAGCGGCCGCGCTCGAGACGGTGACCGTGG
(The underline indicates the NotI site.)

(5) SEQ ID NO: 5
AAAAAAGGCCCAGCCGGCCATGGCGTCGACGGATATTTTGATGAC
(The underline indicates the SfiI site.)

(6) SEQ ID NO: 6
TTTCTCGTGCGGCCGCACGTTTTATTTCCAACTTTG
(The underline indicates the NotI site.)

(A) Construction of Expression Plasmids
(a) Vectors Used in the Experiments pET-MBPp-His6: pET15b vector (Merck Chemicals Ltd., Darmstadt, Germany), into which the gene encoding maltose binding protein (MBP) tagged with His-Tag containing six histidine residues (His6) is inserted (SEQ ID NO: 7).

pIT2-LxE16: pIT2 vector (provided by MRC Cambridge, UK), into which the single-chain antibody (scFv) gene encoding anti-hen egg lysozyme (HEL) antibody LxE16 (isolated at Laboratory of Protein Engineering, Department of Chemistry and Biotechnology, Graduate School of Engineering, University of Tokyo) is inserted (SEQ ID NO: 8, amino acid: SEQ ID NO: 9).

(b) Outline of the Preparation of the Expression Vectors

As shown in the scheme of FIG. 2A, an expression vector pET-MBPp-VH(HEL)-His10 encoding a MBP-VH(HEL)-His10 protein, in which MBP and a His-tag containing ten histidine residues (His10) are respectively fused to N- and C-terminals of VH(HEL) (the heavy-chain variable region domain of the anti-lysozyme antibody LxE16), and an expression vector pET-MBPp-VL(HEL)-His10 encoding a MBP-VL(HEL)-His10 protein, in which MBP and His10 are respectively fused to N- and C-terminals of VL(HEL) (the light-chain variable region domain of the anti-lysozyme antibody LxE16) were constructed by using the pET-MBPp-His6.

First, DNA fragment (1) containing His6 was isolated from the pET-MBPp-His6, and then DNA fragment (2) encoding His10 was inserted thereinto, thereby obtaining a pET-MBPp-His10. Subsequently, a VH(HEL) gene (SEQ ID NO: 10, Table 3) was inserted into the pET-MBPp-His10, thereby obtaining the pET-MBPp-VH(HEL)-His10. Further, a VL(HEL) gene (SEQ ID NO: 11, Table 4) was inserted into the pET-MBPp-His10, thereby obtaining the pET-MBPp-VL(HEL)-His10.

TABLE 3

VH(HEL)

ATGGCCGAGGTGCAGCTTCAGGAGTCAGGACCTAGCCTCGTGAAACCTTC

TCAGACTCTGTCCCTCACCTGTTCTGTCACTGGCGACTCCATCACCAGGG

GTTACTGGAGCTGGATCCGGAAATCCCCAGGAAATAAACTTGAGTACATG

GGGTACATAAGCTACAGTGGTAGCACTTTCTACAATCCATCTCTCAAAAG

TCGAATCTCCATCACTCGAGACACATTCAAGAACCAGCTCTACCTGCAGT

TGAATTCTGTGACTACTGAGGACACAGCCACATATTATTGTGCAGAGTAC

GACGGGACTTACTGGGGCCAAGGGACCACGGTCACCGTCTC

TABLE 4

VL(HEL)

TCGACGGATATTTTGATGACCCAGACTCCAGCCACCCTGTCTGTGACTCC

AGGAGATAGCGTCAGTCTTTCCTGCAGGGCCAGCCAAAGTATTGGCAACA

ACCTACACTGGTTTCAACAAAAATCACATGAGTCTCCAAGGCTTCTCATC

AAGTATGCTTCCCAGTCCATCTCTGGGATCCCCTCCAGGTTCAGTGGCAG

TGGATCAGGGACAGATTTCACTCTCAGTATCAACACTGTGGAGACTGAAG

ATTTTGGAATGTATTTCTGTCAACAGAGTAACAGCTGGCCGTACACGTTC

GGAGGGGGGACAAAGTTGGAAATAAAACGT (b) Isolation of DNA Fragment (1) from the pET-MBPpP-His6

To 74 µl of an aqueous solution containing about 10 µg of pET-MBPp-His6, 3 µl of ScaI (Roche Applied Science, Basel, Switzerland, 10 U), 3 µl of NotI (Roche Applied Science, 10 U), 10 µl of 10×BSA solution and 10 µl of 10× H buffer (Roche Applied Science) were added, and the mixture was then left to stand for about 3 hours at 37° C. Subsequently, the mixture was subjected to electrophoresis on 1% agarose gel (in TAE buffer), and then a DNA band of approximately 4,100 bp was excised and extracted using WIZARD SV Gel And PCR Clean-Up System (trade name, manufactured by Promega Co., Madison, Wis.). The extracted DNA was dissolved in 50 µl of milliQ water.

(c) Preparation of DNA Fragment (2)

PCR was performed by using the pET-MBPp-His6 as the template, a primer (1) (SEQ ID NO: 1) and a primer (2) (SEQ ID NO: 2). The primer (1) is a reverse primer having a nucleic acid sequence corresponding to ten histidine residues and having the NotI site; and an annealing site of the primer (1) is located downstream of the His6 coding region. The primer (2) is a forward primer; and an annealing site of the primer (2) is located approximately 500 bases downstream of the ScaI site of the pET vector.

The PCR conditions are as follows:

| Composition of the reaction mixture | |
|---|---|
| pET-MBPp-His6 (about 100 µg/ml) | 0.5 µl |
| Primer (1) (50 µM) | 0.5 µl |
| Primer (2) (50 µM) | 0.5 µl |
| 10 × Pfu buffer (20 mM Mg$^{2+}$) (Agilent Technologies, Inc., Santa Clara, CA) | 5 µl |
| dNTP Mixture (2.5 mM each) | 4 µl |
| 2.5 U/µl of Pfu DNA polymerase (Agilent Technologies, Inc.) | 0.5 µl |
| milliQ water | 39 µl |
| Reaction cycle | |
| 1. 94° C., 1 min 2. 94° C., 30 sec 3. 58° C., 30 sec 4. 72° C., 30 sec (25 cycles of steps 2 to 4) 5. 72° C., 10 min 6. 16° C. ∞ | |

The PCR product was purified with WIZARD SV Gel And PCR Clean-Up System and dissolved in 50 µl of milliQ water. To the solution, 1 µl of ScaI (Roche Applied Science, 10 U), 1 µl of NotI (Roche Applied Science, 10 U), 7 µl of 10×BSA solution, 7 µl of 10× H buffer (Roche Applied Science) and 4 µl of milliQ water were added, and the mixture was then left to stand for about 3 hours at 37° C. Subsequently, the mixture was subjected to electrophoresis on 1% agarose gel (in TAE buffer), and then a DNA band of approximately 1,080 bp was excised and extracted using WIZARD SV Gel And PCR Clean-Up System (Promega Co., Madison, Wis.). The extracted DNA was dissolved in 50 µl of milliQ water, thereby obtaining a solution of DNA fragment (2).

(d) Preparation of pET-MBPp-His10

0.5 µl of a solution containing the pET-MBPp-His6 from which DNA fragment (1) has been removed and 5 µl of the solution of DNA fragment (2) were mixed. Subsequently, 5.5 µl of DNA LIGATION HIGH Ver2 Solution (trade name, manufactured by TOYOBO CO., LTD., Osaka, Japan) was added to the mixture, and then DNA ligation was performed for 30 minutes at 16° C. Thereafter, about 50 µl of E. coli XL10-Gold chemical competent cells were transformed with about 1 µl of the reaction mixture. The transformants were cultured on LBAG agar medium overnight at 37° C. A single-colony transformant was further cultured in 50 ml of LBAG overnight, and then the plasmid DNA was extracted using WIZARD PLUS MINIPREPS DNA Purification Kit (trade name, manufactured by Promega Co.), thereby obtaining pET-MBPp-His10. The DNA sequence encoding His10 was confirmed in accordance with a protocol from Beckman Coulter, Inc.

(e) Restriction Enzyme Treatment of pET-MBPp-His10

To 46 µl of an aqueous solution containing about 7 µg of pET-MBPp-His10, 2 µl of SfiI (Roche Applied Science, 10 U), 6 µl of 10×BSA solution and 6 µl 10× M buffer (Roche Applied Science) were added, and the mixture was then left to stand for about 3 hours at 50° C. DNA was purified using WIZARD SV Gel And PCR Clean-Up System and then dissolved in 50 µl of an aqueous solution. To the DNA solution, 2 µl of NotI (Roche Applied Science, 10 U), 7 µl of 10×BSA solution, 7 µl of 10× H buffer (Roche Applied Science) and 4 µl of milliQ water were added, and the mixture was then left to for about 3 hours stand at 37° C. Subsequently, the mixture was subjected to electrophoresis on 1% agarose gel (in TAE buffer), and then a DNA band of approximately 4,800 bp was excised and extracted using WIZARD SV Gel And PCR Clean-Up System. The extracted DNA was dissolved in 50 µl of milliQ water.

(f) Preparation of the VH(HEL) Gene Fragment

PCR amplification of the VH(HEL) gene fragment was performed by using pIT2-LxE16 as a template, and a primer (3) and a primer (4). The primer (3) is a reverse primer having a SfiI site; and an annealing site of the primer (3) is located at the 5' side of the VH(HEL) gene fragment. The primer (4) is a forward primer having the NotI site; and an annealing site of the primer (4) is located at the 3' side of the VH(HEL) gene fragment.

The PCR conditions are as follows:

| Reaction mixture composition | |
|---|---|
| pIT2-LxE16 (about 100 µg/ml) | 0.5 µl |
| Primer (3) (50 µM) | 0.5 µl |
| Primer (4) (50 µM) | 0.5 µl |
| 10 × Pfu buffer (20 mM Mg$^{2+}$) (Agilent Technologies, Inc.) | 5 µl |
| dNTP Mixture (2.5 mM each) | 4 µl |
| 2.5 U/µl of Pfu DNA polymerase (Agilent Technologies, Inc.) | 0.5 µl |
| milliQ water | 39 µl |

| Reaction cycle |
|---|
| 1. 94° C., 1 min |
| 2. 94° C., 30 sec |
| 3. 58° C., 30 sec |
| 4. 72° C., 30 sec |
| (25 cycles of steps 2 to 4) |
| 5. 72° C., 10 min |
| 6. 16° C. ∞ |

The PCR product was purified with WIZARD SV Gel And PCR Clean-Up System and dissolved in 50 µl of milliQ water. To the solution, 2 µl of SfiI (Roche Applied Science, 10 U/µl), 7 µl of 10×BSA solution, 7 µl of 10× M buffer (Roche Applied Science) and 4 µl of milliQ water were added, and the mixture was then left to stand for about 3 hours at 50° C. The resulting DNA was purified with WIZARD SV Gel And PCR Clean-Up System and dissolved in 50 µl of aqueous solution. To the DNA solution, 2 µl of NotI (Roche Applied Science, 10 U), 7 µl of 10×BSA solution, 7 µl of 10× H buffer (Roche Applied Science) and 4 µl of milliQ water were added, and the mixture was then left to stand for about 3 hours at 37° C. Subsequently, the resulting DNA was purified with WIZARD SV Gel And PCR Clean-Up System. The extracted DNA was dissolved in 50 µl of milliQ water, thereby obtaining a solution of the VH(LxE16) gene fragment.

(g) Preparation of the VL(HEL) Gene Fragment

PCR amplification of the VL(HEL) gene fragment was performed by using pIT2-LxE16 as a template, and a primer (5) and a primer (6). The primer (5) is a reverse primer having a SfiI site; and an annealing site of the primer (5) is located at the 5' side of the VL(HEL) gene fragment. The primer (6) is a forward primer having a NotI site; and an annealing site of the primer (6) is located at the 3' side of the VL(HEL) gene fragment. PCR, restriction enzyme treatment and purification of DNA were performed in the same manner as in preparation of VH(LxE16) gene fragment, thereby obtaining a solution of the VL(LxE16) gene fragment.

(h) Preparation of the pET-MBPp-VH(HEL)-His10 and the pET-MBPp-VL(HEL)-His10

0.5 µl of a solution containing the restriction enzyme treated pET-MBPp-His10 was mixed with 5 µl of a solution of VH(LxE16) or VL(LxE16). Subsequently, 5.5 µl of DNA LIGATION HIGH Ver2 Solution (TOYOBO CO.) was added to the mixture, and then DNA ligation was performed for 30 minutes at 16° C. Thereafter, about 50 µl of *E. coli* XL10-Gold chemical competent cells were transformed with about 1 µl of the reaction mixture. The transformants were cultured on LBAG agar medium overnight at 37° C. Single colony transformants were further cultured in 50 ml of LBAG overnight, and then the plasmid DNA was extracted using WIZARD PLUS MINIPREPS DNA Purification Kit (Promega Co.). The DNA sequences of pET-MBPp-VH(HEL)-His10 and pET-MBPp-VL(HEL)-His10 were confirmed in accordance with a protocol from Beckman Coulter, Inc.

(B) Preparation of the MBP-VH(HEL)-His10 Protein and the MBP-VL(HEL)-His10 Protein The pET-MBPp-VH(HEL)-His10 and pET-MBPp-VL (HEL)-His10 plasmids were respectively transformed into *E. coli* OverExpress C41(DE3) by the heat shock method to express the genes. One µl of the plasmid (about 100 ng) and 100 µl of OverExpress C41(DE3) competent cells were mixed, and the mixture was then left to stand for 30 min on ice. Subsequently, heat shock was performed for 45 seconds at 42° C. Immediately after the heat shock, the mixture was left to stand for 2 minutes on ice. Thereafter, the cells were cured for 30 minutes by adding 200 µl of SOC medium thereto. The mixture was then spread on LBA plate and incubated overnight at 37° C.

A grown colony was inoculated into 4 ml of LBAG and cultured overnight at 30° C. with shaking. 4 ml of the small-scale culture was then added to 800 ml of LBA, and cultured at large scale at 30° C. with shaking. When an O.D. 600 of the culture reached between 0.5 and 0.6, 400 µl of 1000 mM IPTG was added thereto and further cultured overnight at 30° C. with shaking. The bacterial culture was then separated into supernatants and pellets of *E. coli* by centrifugation. By the methods described below, the MBP-VH(HEL)-His10 protein (SEQ ID NO: 12, Table 5) was independently collected from the supernatants by ammonium sulfate precipitation and from the pellet by ultrasonication of bacterial cells. Further, by the methods described below, the MBP-VL(HEL)-His10 protein (SEQ ID NO: 13, Table 6) was independently collected from the supernatants by ammonium sulfate precipitation and from the pellet by ultrasonication of bacterial cells.

TABLE 5

| MBP-VH(HEL)-His10 |
|---|
| MKIKTGARILALSALTTMMFSASALAKIEEGKLVIWINGDKGYNGLAEVGKKFEKDTGIKV |
| TVEHPDKLEEKFPQVAATGDGPDIIFWAHDRFGGYAQSGLLAEITPDKAFQDKLYPFTW |

TABLE 5-continued

MBP-VH(HEL)-His10

DAVRYNGKLIAYPIAVEALSLIYNKDLLPNPPKTWEEIPALDKELKAKGKSALMFNLQEPY

FTWPLIAADGGYAFKYENGKYDIKDVGVDNAGAKAGLTFLVDLIKNKHMNADTDYSIAE

AAFNKGETAMTINGPWAWSNIDTSKVNYGVTVLPTFKGQPSKPFVGVLSAGINAASPNK

ELAKEFLENYLLTDEGLEAVNKDKPLGAVALKSYEEELAKDPRIAATMENAQKGEIMPNI

PQMSAFWYAVRTAVINAASGRQTVDEALKDAQTNSSSNNNNNNNNNNLGPGAAHY--

VEFAAQPAMADVELQESGPSLVKPSQTLSLTCSVTGDSITRGYWSWIRKFPGNKLEYM

GYISYSGSTFYNPSLKSRISITRDTFKNQLYLQLNSVTTEDTATYYCAEYDGTYWGQGTT

VTVSSAAAEHHHHHHHHHH

-: Protease cleavage site

TABLE 6

MBP-VL(HEL)-His10

MKIKTGARILALSALTTMMFSASALAKIEEGKLVIWINGDKGYNGLAEVGKKFEKDTGIKVT

VEHPDKLEEKFPQVAATGDGPDIIFWAHDRFGGYAQSGLLAEITPDKAFQDKLYPFTWDA

VRYNGKLIAYPIAVEALSLIYNKDLLPNPPKTWEEIPALDKELKAKGKSALMFNLQEPYFT

WPLIAADGGYAFKYENGKYDIKDVGVDNAGAKAGLTFLVDLIKNKHMNADTDYSIAEAAF

NKGETAMTINGPWAWSNIDTSKVNYGVTVLPTFKGQPSKPFVGVLSAGINAASPNKELA

KEFLENYLLTDEGLEAVNKDKPLGAVALKSYEEELAKDPRIAATMENAQKGEIMPNIPQM

SAFWYAVRTAVINAASGRQTVDEALKDAQTNSSSNNNNNNNNNNLGPGAAHY--

VEFAAQPAMASTDILMTQTPATLSVTPGDSVSLSCRASQSIGNNLHWFQQKSHESPRLLI

KYASQSISGIPSRFSGSGSGTDFTLSINTVETEDFGMYFCQQSNSWPYTFGGGTKLEIKR

AAAEHHHHHHHHHH

-: Protease cleavage site

In the case of using the supernatant, 344 g of ammonium sulfate was added to about 800 ml of the culture supernatant and the mixture was stirred overnight at 4° C. Subsequently, an insoluble matter containing MBP-VH(HEL)-His10 or MBP-VL(HEL)-His10 was collected by centrifugation and the pellet was suspended in 30 ml of TALON Buffer. In the case of using the pellet of $E.$ $coli$, the pellet was suspended in 30 ml of TALON Buffer and then subjected to ultrasonication, followed by centrifugation, to collect a supernatant containing MBP-VH(HEL)-His10 or MBP-VL(HEL)-His10. The supernatant was dialyzed against the TALON Buffer. Each protein collected in TALON Buffer was applied to a column (16 mm-diameter×about 15 mm-height) filled with a TALON Affinity Resin (trade name, manufactured by Clontech Laboratories, Inc., Mountain View, Calif.). Subsequently, TALON Affinity Resin, onto which the protein was adsorbed, was washed with the TALON Buffer, and then a TALON Elution Buffer was added to elute MBP-VH(HEL)-His10 or MBP-VL(HEL)-His10. The purified protein was confirmed by SDS-PAGE. The buffer of the eluate was changed to HBS-N, and then glycerol was added thereto at a final concentration of 16%. The obtained solution was stored at −80° C.

(C) Preparation of VL(HEL)-His10

To 1 ml of the purified MBP-VL(HEL)-His10 solution (in HBS-N, about 1000 μg/ml), 20 μl of GENENASE solution (New England Biolabs, Inc., Ipswich, Mass.) was added. The mixture was allowed to react at room temperature for about 5 hours. After the reaction, in the same manner as described above, VL(HEL)-His10 was purified using the TALON Affinity Resin and the buffer of the eluate was changed to HBS-N.

(2) Fabrication of a Substrate Provided with a Carboxyl Group

SENSORCHIP AU (trade name, manufactured by GE Healthcare), in which only a gold film had been formed on the sensor chip, was subjected to a UV/ozone treatment for 12 minutes. Subsequently, 9.5 ml of an ethanol solution dissolving 9.5 μmol of Carboxy-ED$_6$-undecanethiol (manufactured by Dojindo Laboratories) was mixed with 9 ml of an ethanol solution dissolving 9 μmol of Hydroxy-ED$_3$-undecanethiol (manufactured by Dojindo Laboratories) in the ratio of 1:9. The gold film was allowed to react with the mixed solution for 12 hours at 40° C. to form a polymer on the gold film. The resultant was washed twice with ethanol, thereby obtaining a substrate sample.

(3) Formation of the Complex

MBP-VH(HEL)-His10 and VL(HEL)-His10, both of which were prepared above, and lysozyme were mixed in a number ratio of 1:1:1 to prepare a 3.18 µM each solution in HEPES buffer. The mixed solution was then left to stand for 3 hours at room temperature, thereby obtaining a complex sample solution.

(4) Immobilization of the Complex

The substrate sample prepared above was set in a surface plasmon resonance analyzer (trade name: BIACORE 3000, manufactured by Biacore). The substrate surface was stabilized with HEPES buffer solution for SPR (20 mM HEPES-HCl, 150 mM NaCl, pH7.4) at a flow rate of 10 µl/min, and then 70 µl of a mixed aqueous solution of 0.2 mM of 1-(3-dimethylaminopropyl)-3-ethylcarbodiimide (EDC) and 0.04 mM N-hydroxysuccinimide (NHS) was injected thereonto. Thereafter, 50 µl of a two-fold dilution of the above complex sample solution with an acetate buffer (pH 4.5) was injected onto the substrate sample, and then blocking treatment was performed with an ethanolamine solution.

(5) Washing of the Antigen

After immobilization of the complex, the substrate was subjected to 1-minute washing for five times by alternately using a glycine buffer (pH 1.5) and 10 mM NaOH to remove the antigen, thereby obtaining an immobilization substrate A of Example 1. The immobilization amount of the antibody fragments was calculated based on the refractive index of the sample after the washing and the refractive index of the sample prior to the immobilization of the complex.

(6) Evaluation of a Binding Reaction with the Antigen 100 nM lysozyme was injected onto the immobilization substrate A obtained above over 10 minutes, and the binding amount of lysozyme was evaluated.

Example 2

An immobilization substrate B was prepared in the same manner as in Example 1, except that commercially available SENSORCHIP CM5 (trade name, manufactured by GE Healthcare; carboxymethyl dextran coupled type) was used in place of SENSORCHIP AU. The binding amount of lysozyme in the immobilization substrate B was evaluated in the same manner as in Example 1.

Example 3

An immobilization substrate C was prepared in the same manner as in Example 1, except that the mixing ratio among MBP-VH(HEL)-His10, VL(HEL)-His10, and lysozyme in formation of the complex of Example 2 was changed to 10:10:1. The binding amount of lysozyme in the immobilization substrate C was evaluated in the same manner as in Example 1.

Comparative Example 1

To the substrate sample obtained in process (2) of Example 1, MBP-VH(HEL)-His10 and VL(HEL)-His10 were immobilized in this order in the same manner as in process (4) of Example 1, and then the resulting immobilization substrate was washed in the same manner as in process (5) of Example 1, thereby obtaining an immobilization substrate D of Comparative Example 1. Thereafter, in the same manner as in process (6) of Example 1, the binding amount of lysozyme in the immobilization substrate D was evaluated.

Comparative Example 2

To commercially available SENSORCHIP CM5 (trade name, manufactured by GE Healthcare), MBP-VH(HEL)-His10 and VL(HEL)-His10 were immobilized in this order in the same manner as in process (4) of Example 1, and the resulting immobilization substrate was washed in the same manner as in process (5) of Example 1, thereby obtaining an immobilization substrate E of Comparative Example 2. Thereafter, in the same manner as in process (6) of Example 1, the binding amount of lysozyme in the immobilization substrate E was evaluated.

Comparative Example 3

An immobilization substrate F of Comparative Example 3 was obtained in the same manner as in Comparative Example 2, except that, in the immobilization of the complex, MBP-VH(HEL)-His10, VL(HEL)-His10 and lysozyme were mixed to perform immobilization, and the resulting immobilization substrate was washed in the same manner as in process (5) of Example 1. Thereafter, in the same manner as in process (6) of Example 1, the binding amount of lysozyme in the immobilization substrate F was evaluated.

Evaluation

Measurement of the Binding Ratio of Lysozyme

Based on the results obtained in Examples 1 to 3 and Comparative Examples 1 to 3, the binding ratio of lysozyme was calculated and compared. Time-dependent change in binding over a period of 10 minutes from starting the addition of lysozyme was measured using BIACORE 3000. The binding ratio of lysozyme was obtained by dividing the binding amount of lysozyme during the 10-minutes-period by the immobilization amount of the antibody fragments. The binding amount of lysozyme was calculated and expressed as a relative value, assuming that the binding amount of lysozyme in Comparative Example 2 is 1.

The results are shown in Table 7.

Antigen Binding Ratio Against the Ideal Antigen Binding Amount

To each of the immobilization substrates C and F obtained in Example 3 and Comparative Example 3, respectively, 100 nM lysozyme was added for 10 minutes and a binding amount of lysozyme was measured. The antigen binding ratio was obtained based on the binding amount, whereby the ideal antigen-binding amount was 286 RU assuming that the immobilization amount of MBP-VH(HEL)-His10 and VL(HEL)-His10 is 0.025 pmol/mm$^2$.

The results are shown in Table 7.

TABLE 7

| | Immobilization substrate | Antigen binding ratio (%) | Lysozyme binding ratio | Immobilization amount (pg/mm$^2$) |
| --- | --- | --- | --- | --- |
| Example 1 | A | — | 10.8 | 1089 |
| Example 2 | B | — | 14.5 | 1618 |
| Example 3 | C | 28.4 | 17.4 | 1400 |
| Comparative Example 1 | D | — | 2.5 | 1573 |
| Comparative Example 2 | E | — | 1 | 2516 |
| Comparative Example 3 | F | 0.6 | 0.8 | 3297 |

As is apparent from Table 7, in the immobilization substrates (Comparative Examples 1, 2, and 3), each of which was prepared without forming the complex between the antibody fragments and the antigen and in which the positions of the antibody fragments on the substrate are not controlled, the binding ratio of lysozyme, that is, the binding ability to the lysozyme is low. On the other hand, each of the immobilization substrates of Examples 1, 2 and 3 exhibits a higher lysozyme binding ratio. Therefore, according to the present invention, the reaction of the complex composed of three or more substances can be efficiently detected, and detection sensitivity and accuracy can be improved.

In addition, in Example 3, in which the mixing ratio among anti-lysozyme VH-region polypeptide, anti-lysozyme VL-region polypeptide and lysozyme is 10:10:1, a high binding amount is obtained, which shows that a higher binding ratio can be obtained even when the mixing ratio thereof is not equal.

Example 4

(1) Preparation of the VH(HEL)-His6 Protein

The pIT2-LxE16 plasmid was transformed into *E. coli* HB2151 by heat shock method for the expression. 1 µl of the plasmid (about 100 ng) and 100 µl of HB2151 competent cells were mixed, and the mixture was then left to stand for 30 min on ice. Subsequently, heat shock was performed for 45 seconds at 42° C. Immediately after the heat shock, the mixture was left to stand for 2 minutes on ice. Thereafter, the cells were cured for 30 minutes by adding 200 µl of SOC medium thereto. The mixture was then spread on an LBA plate and incubated overnight at 37° C.

A grown colony was inoculated into 4 ml of LBAG and cultured overnight at 30° C. with shaking. 4 ml of the small-scale culture was then added to 800 ml of LBA, and cultured at large scale at 30° C. with shaking. When an O.D. 600 reached between 0.5 and 0.6, 400 µl of 1000 mM IPTG was added thereto and further cultured overnight at 16° C. with shaking. The bacterial culture was separated into supernatants and pellets of *E. coli* by centrifugation. By the methods described below, the VH(HEL)-His6 protein (SEQ ID NO: 14, Table 8) was independently collected from the supernatants by ammonium sulfate precipitation and from the pellet by ultrasonication of bacterial cells.

In the case of using the supernatant, 344 g of ammonium sulfate was added to about 800 ml of the culture supernatant, and the mixture was stirred overnight at 4° C. Subsequently, an insoluble matter containing VH(HEL)-His6 was collected by centrifugation, and the pellet was suspended in 30 ml of TALON Buffer. In the case of using the pellet of *E. coli*, the pellet was suspended in 30 ml of TALON Buffer and then subjected to ultrasonication, followed by centrifugation, to collect a supernatant containing VH(HEL)-His6. The supernatant was dialyzed against the TALON Buffer. Each protein collected in TALON Buffer was applied to a column (16 mm-diameter×about 15 mm-height) filled with a TALON Affinity Resin (trade name, manufactured by Clontech Laboratories, Inc., Mountain View, Calif.). Subsequently, TALON Affinity Resin, onto which the protein was adsorbed, was washed with the TALON buffer. Thereafter, a TALON Elution Buffer was added to elute VH(HEL)-His6. The purified protein was confirmed by SDS-PAGE. The buffer of the eluate was changed to HBS-N, and then glycerol was added thereto at a final concentration of 16%. The obtained solution was stored at −80° C.

TABLE 8

VH(HEL)-His6

EVQLQESGPSLVKPSQTLSLTCSVTGDSITRGYWSWIRKFPGNKLEYMG

YISYSGSTFYNPSLKSRISITRDTFKNQLYLQLNSVTTEDTATYYCAEY

DGTYWGQGTTVTVHHHHHHGAAEQKLISEEDLNGAA (2) Formation of the Complex and Evaluation of Binding An immobilization substrate G was obtained in the same manner as in Example 1, except that the mixing ratio among VH(HEL)-His6 obtained above, VL(HEL)-His10, and lysozyme in formation of the complex was changed to 10:10:3. The binding amount of lysozyme in the immobilization substrate G was evaluated in the same manner as in Example 1.

Comparative Example 4

An immobilization substrate H was obtained in the same manner as in Example 4, except that, in the immobilization of the complex, VH(HEL)-His6 obtained above and VL(HEL)-His10 were immobilized in this order. The binding amount of lysozyme in the immobilization substrate H was evaluated in the same manner as in Example 1.

Evaluation

Measurement of the Binding Ratio of Lysozyme

Based on the results obtained in Example 4 and Comparative Example 4, the binding ratio of lysozyme was calculated and compared. Time-dependent change in lysozyme binding over a period of 10 minutes from starting the addition of lysozyme was measured using BIACORE 3000. The binding ratio of lysozyme was obtained by dividing the binding amount of lysozyme during the 10-minutes-period by the immobilization amount of the antibody fragments.

The binding amount of lysozyme was calculated and expressed as a relative value, assuming that the binding amount of lysozyme in Comparative Example 2 is 1.

TABLE 9

| | Immobilization substrate | Lysozyme binding ratio | Immobilization amount (pg/mm²) |
|---|---|---|---|
| Example 4 | G | 7.6 | 977 |
| Comparative Example 4 | H | 1 | 1631 |

As is apparent from Table 9, even when the antibody fragment is not in the form of the MBP fusion product, the reaction of a complex composed of three or more substances can be efficiently detected, and detection sensitivity and accuracy can be improved.

In addition, comparison of the binding rate of lysozyme in Example 4 with that in Example 3, in which one of the single chain peptides is the MBP fusion product, based on the binding amount per unit time revealed that the binding rate in Example 4 was higher than that of Example 3. Accordingly, it is considered that the VH-region and VL-region polypeptides of Example 4, each of which has a lower molecular weight, can change their position to the optimal position for binding to lysozyme in a shorter time when cooperatively binding to lysozyme. Therefore, it is thought that a distance among the antibody fragments is not always zero (in other words, a state wherein the antibody fragments bind to one another).

Due to the above, it is thought that the immobilization substrate according to the present invention can be applied to a catalytic reaction, sequential reaction or the like, in which the flexibility of a substance is critical. It is thought that, in many cases, for such an application to a catalytic reaction, a sequential reaction or the like, using the VH-region and VL-region polypeptides having a weaker affinity is more advantageous compared with using the VH-region and VL-region polypeptides having a greater affinity.

Example 5

Preparation of anti-osteocalcin (BGP) VH-region polypeptide (VH(BGP)), and a fusion protein of VH(BGP) with MBP (MBP-VH(BGP)), and a fusion protein of anti-BGP VL-region polypeptide with MBP (MBP-VL(BGP))

Abbreviations used in the Examples below are as follow:

LB: Same as that used in Example 1
LBA: Same as that used in Example 1
LBAG: Same as that used in Example 1
LBA plate: Same as that used in Example 1
SOC: Same as that used in Example 1
PBS: 10 mM phosphate buffer (pH 7.2) containing 137 mM NaCl and 2.7 mM KCl
5% IBPBS: PBS containing 5% (v/v) of IMMONOB-LOCK (trade name, manufactured by Dainippon Sumitomo Pharma Co., Ltd., Osaka)
20% IBPBS: PBS containing 20% (v/v) IMMONOB-LOCK
PBST: PBS containing 0.1% of Triton-X 100
TAE buffer: Same as that used in Example 1
TALON Buffer: Same as that used in Example 1
TALON Elution Buffer: Same as that used in Example 1
IPTG: Same as that used in Example 1
HBS-N buffer: Same as that used in Example 1

Similarly to Example 1, water purified with MILLI-Q (trade name, manufactured by Millipore Co., Billerica, Mass.) was used in all experiments. Hereinafter the purified water is referred to as milliQ water. Unless otherwise specified, general reagents used were obtained from Sigma-Aldrich Co. (St. Louis, Mo., USA), Nacalai Tesque (Kyoto, Japan), Wako Pure Chemical Industries, Ltd. (Osaka, Japan), or Kanto Chemical Co. Inc. (Tokyo, Japan). Oligo DNAs were synthesized by Texas Genomics Japan (Tokyo, Japan) or Invitrogen (Tokyo, Japan).

The genotypes of the *E. coli* XL10-Gold, OverExpress C41, and HB2151 are shown in Table 10.

TABLE 10

XL-10 gold: Tetr Δ(mcrA) 183, Δ(mcrCB-hsdSMR-mrr) 173, endA1, supE44, thi-1, recA1, gyrA96, relA1, lac, Hte[F′ proAB, lacIq, ZΔM15, Tn10(Tetr), Tn5(Kanr), Amy]
OverExpress C41(DE3): F−, ompT, hsdSB(rB− mB−), gal(λcI 857, ind1, Sam7, nin5, lacUV5-T7 gene1), dcm(DE3)
HB2151: K12d(lac-pro), thi/F′; pro A+B+, Lac IqZ dM15)

(A) Construction of the Expression Plasmid for MBP-VH (BGP)

(a) Vectors Used in the Experiments pET-MBPp-His6: pET15b vector (provided by Merck Chemicals Ltd., Darmstadt, Germany), into which the gene encoding maltose binding protein (MBP) tagged with His-Tag containing six histidine residues (His6) is inserted (described above, SEQ ID NO: 7).

pIT2-VH(BGP): pIT2 vector, into which the gene encoding a VH-region polypeptide of anti-BGP antibody (VH (BGP)) (SEQ ID NO: 15, Table 11, amino acid: SEQ ID NO: 16) is inserted.

pMAL-VL(BGP): an expression vector for a fusion protein of a VL-region polypeptide of anti-BGP antibody KTM219 and MBP (MBP-VL(BGP)) (described in, Lim et al. Anal. Chem. 79, 6193(2007)).

TABLE 11

| VH (BG P) |
|---|
| GAGGTACAGCTGGAGGAGTCTGGGGCTGAGTTTGTGAAGGCTGGGGCTTC |
| AGTGAAGCTGTCCTGCAAGACTTCTGGCTACACCTTCAACAACTACTGGA |
| TTCACTGGGTCAAACAGAGCCCAGGACAAGGCCTTGAATGGATCGGAGAA |
| ATTGATCCCTCTGATGGTTATTCTAACTACAATCAAAAATTCAAGGGCAA |
| GGCCACATTGACTGTGGACAAGTCCTCCAGCACTGCCTACATGCACCTCA |
| ACAGTCTGACTTCTGAGGACTCTGCGGTCTATTATTGTACAAGCAGCACT |
| TCGGTAGGAGGTTCCTGGGGCCAAGGGACCACGGTCACCGTCTCGAGC |

(b) Restriction Enzyme Treatment of pET-MBPp-His6

To 77 μl of an aqueous solution containing about 10 μg of pET-MBPp-His6, 3 μl of NotI (Roche Applied Science, Basel, Switzerland, 10 U), 10 μl of 10×BSA solution and 10 μl 10× H buffer (Roche Applied Science) were add, and the mixture was then left to stand for about 3 hours at 37° C. Subsequently, DNA was purified using WIZARD SV Gel And PCR Clean-Up System (trade name, manufactured by Promega Co., Madison, Wis.) and dissolved in 50 μl of milliQ water. To the solution, 3 μl of SfiI (Roche Applied Science, 10 U), 7 μl of 10×BSA solution and 7 μl of 10× M buffer (Roche Applied Science) were added, and the mixture was then left to stand for about 3 hours at 50° C. Subsequently, the mixture was subjected to electrophoresis on 1% agarose gel (in TAE buffer), and then a DNA band of approximately 4,100 bp was excised and extracted using WIZARD SV Gel And PCR Clean-Up System (Promega Co.). The extracted DNA was dissolved in 50 μl of milliQ water.

(c) Isolation of VH(BGP) Gene Fragment from the pIT2-VH(BGP)

To 77 μl of an aqueous solution containing about 10 μg of pIT2-VH(BGP), 3 μl of NotI (Roche Applied Science, 10 U), 10 μl of 10×BSA solution and 10 μl 10× H buffer (Roche Applied Science) were added, and the mixture was then left to stand for about 3 hours at 37° C. Subsequently, DNA was purified using WIZARD SV Gel And PCR Clean-Up System (Promega Co.) and the purified DNA was dissolved in 50 μl of milliQ water. To the DNA solution, 3 μl of SfiI (Roche Applied Science, 10 U), 7 μl of 10×BSA solution, and 7 μl of 10× M buffer (Roche Applied Science) were added and the mixture was then left to stand for about 3 hours at 50° C. Subsequently, the mixture was subjected to electrophoresis on 1% agarose gel (in TAE buffer), and then a DNA band of approximately 450 bp was excised and extracted using WIZARD SV Gel And PCR Clean-Up System (Promega Co.). The extracted DNA was dissolved in 50 µl of milliQ water.

(d) Incorporation of VH(BGP) into the pET-MBPp-His6

0.5 µl of a solution containing pET-MBPp-His6, which was treated with the restriction enzymes and purified as described above, and 5 µl of a solution of VH(BGP), which was treated with the restriction enzymes and purified as described above, were mixed. Subsequently, 5.5 µl of DNA LIGATION HIGH Ver2 Solution (TOYOBO CO., LTD., Osaka) was added to the mixture, and then DNA ligation was performed for 30 minutes at 16° C. Thereafter, about 50 µl of E. coli XL10-Gold chemical competent cells were transformed with about 1 µl of the ligation reaction mixture. The transformants were cultured on a LBAG agar medium overnight at 37° C. A single-colony transformant was further cultured in 50 ml of LBAG overnight. The plasmid DNA was then extracted using WIZARD PLUS MINIPREPS DNA Purification Kit (Promega Co.), thereby obtaining pET-MBPp-VH(BGP). The DNA sequence of pET-MBPp-VH(BGP) was confirmed in accordance with a protocol from Beckman Coulter, Inc.

(B) Preparation of the MBP-VH(BGP) Protein and the MBP-VL(BGP) Protein

The pET-MBPp-VH(BGP) plasmid and the pMAL-VL (BGP) plasmid were respectively transformed into E. coli OverExpress C41(DE3) by heat shock method for the expression. 1 µl of the plasmid (about 100 ng) and 100 µl of OverExpress C41(DE3) competent cells were mixed, and the mixture was then left to stand for 30 min on ice. Subsequently, heat shock was performed for 45 seconds at 42° C. Immediately after the heat shock, the resultant was left to stand for 2 minutes on ice. Thereafter, the cells were cured for 30 minutes by adding 200 µl of SOC medium thereto. The mixture was then spread on an LBA plate and incubated overnight at 37° C.

A grown colony was inoculated into 4 ml of LBAG and cultured overnight at 30° C. with shaking. 4 ml of the small-scale culture was then added to 800 ml of LBA, and cultured at large scale at 30° C. with shaking. When an O.D. 600 of the culture reached between 0.5 and 0.6, 400 µl of 1000 mM IPTG was added thereto and further cultured overnight at 20° C. with shaking. The bacterial culture was then separated into supernatants and pellets of E. coli by centrifugation. By the methods described below, each of the MBP-VH(BGP) protein (SEQ ID NO: 17, Table 12) was independently collected from the supernatants by ammonium sulfate precipitation method and from the pellet by ultrasonication of bacterial cells. Further, the MBP-VL (BGP) protein (SEQ ID NO: 18, Table 13) was independently collected from the supernatants by ammonium sulfate precipitation method and from the pellet by ultrasonication of bacterial cells.

TABLE 12

| MBP-VH(BGP) |
| --- |
| MKIKTGARILALSALTTMMFSASALAKIEEGKLVIWINGDKGYNGLAEVGKKFEKDTGIKVT |
| VEHPDKLEEKFPQVAATGDGPDIIFWAHDRFGGYAQSGLLAEITPDKAFQDKLYPFTWD |
| AVRYNGKLIAYPIAVEALSLIYNKDLLPNPPKTWEEIPALDKELKAKGKSALMFNLQEPYFT |
| WPLIAADGGYAFKYENGKYDIKDVGVDNAGAKAGLTFLVDLIKNKHMNADTDYSIAEAAF |
| NKGETAMTINGPWAWSNIDTSKVNYGVTVLPTFKGQPSKPFVGVLSAGINAASPNKELA |
| KEFLENYLLTDEGLEAVNKDKPLGAVALKSYEEELAKDPRIAATMENAQKGEIMPNIPQM |
| SAFWYAVRTAVINAASGRQTVDEALKDAQTNSSSNNNNNNNNNNLGPGAAHYVEFAAQ |
| PAEVQLEESGAEFVKAGASVKLSCKTSGYTFNSYWIHWIKQSPGQGLEWIGEIDPSDGY |
| TNYNQKFKGKATLTVDKSSSTAYMRLNSLTSEDSAVYYCTSSTSVGGSWGQGTTVTVS |
| SHHHHHH |

TABLE 13

| MBP-VL(BGP) |
| --- |
| MKIKTGARILALSALTTMMFSASALAKIEEGKLVIWINGDKGYNGLAEVGKKFEKDTGIKVT |
| VEHPDKLEEKFPQVAATGDGPDIIFWAHDRFGGYAQSGLLAEITPDKAFQDKLYPFTWDA |
| VRYNGKLIAYPIAVEALSLIYNKDLLPNPPKTWEEIPALDKELKAKGKSALMFNLQEPYFTW |
| PLIAADGGYAFKYENGKYDIKDVGVDNAGAKAGLTFLVDLIKNKHMNADTDYSIAEAAFNK |
| GETAMTINGPWAWSNIDTSKVNYGVTVLPTFKGQPSKPFVGVLSAGINAASPNKELAKEF |
| LENYLLTDEGLEAVNKDKPLGAVALKSYEEELAKDPRIAATMENAQKGEIMPNIPQMSAF |
| WYAVRTAVINAASGRQTVDEALKDAQTNSSSNNNNNNNNNNLGIEGRISEFASTDIELTQ |

TABLE 13-continued

MBP-VL(BGP)

SPLSLPVSLGDQASISCTSSQSLLHSNGDTYLHWYLQKPGQSPKLLIYTLSNRFSGVPDRF

SGSGSGTDFTLKISRVEAADLGIYFCSQTTHVPYTFGGGTKLEIKRHHHHHHGAAEQKLIS

EEDLNGAA

In the case of using the supernatant, 344 g of ammonium sulfate was added to about 800 ml of the culture supernatant, and the mixture was stirred overnight at 4° C. Subsequently, an insoluble matter containing MBP-VH(BGP) or MBP-VL (BGP) was collected by centrifugation, and the pellet was suspended in 30 ml of TALON Buffer. In the case of using the pellet of E. coli, the pellet was suspended in 30 ml of TALON Buffer and then subjected to ultrasonication, followed by centrifugation, to collect a supernatant containing MBP-VH(BGP) or MBP-VL(BGP). The supernatant was dialyzed against the TALON Buffer. Each protein collected in TALON Buffer was applied to a column (16 mm-diameter×about 15 mm-height) filled with a TALON Affinity Resin (Clontech Laboratories, Inc., Mountain View, Calif.). Subsequently, TALON Affinity Resin, onto which the protein was adsorbed, was washed with the TALON Buffer, and then a TALON Elution Buffer was added to elute MBP-VH (BGP) or MBP-VL(BGP). The purified protein was confirmed by SDS-PAGE. The buffer of the eluate was changed to HBS-N, and then glycerol was added thereto at a final concentration of 16%. The obtained solution was stored at −80° C.

(C) Formation of the Complex

MBP-VH(BGP) and MBP-VL(BGP), both of which were prepared above, and the C-terminal heptapeptide fragment of BGP (RRFYGPY: SEQ ID NO: 19) were mixed at a number ratio of 1:1:1 to prepare 1.1 µM each solution in HEPES buffer. The mixed solution was then left to stand for 3 hours at room temperature, thereby obtaining a complex sample solution.

(D) Immobilization of the Complex

Commercially available SENSORCHIP CM5 (trade name, manufactured by GE Healthcare) was set in a Surface Plasmon Resonance Analyzer (trade name: BIACORE 3000, manufactured by Biacore). The substrate surface was stabilized with HEPES buffer solution for SPR (20 mM HEPES-HCl, 150 mM NaCl, pH 7.4) at a flow rate of 10 µl/min, and then 70 µl of a mixed aqueous solution of 0.2 mM EDC and 0.04 mM NHS was injected thereonto. Thereafter, 50 µl of a two-fold dilution of the above complex sample solution with an acetate buffer (pH 4.5) was injected onto the substrate sample, and then blocking treatment was performed with an ethanolamine solution.

(E) Washing of the Antigen

After immobilization of the complex, the substrate was subjected to 1-minute washing for five times by alternately using a glycine buffer (pH 1.5) and 10 mM NaOH to remove the antigen, thereby obtaining an immobilization substrate I of Example 5. The immobilization amount of the antibody fragments was calculated based on the refractive index of the sample after the washing and the refractive index of the sample prior to the immobilization of the complex.

(F) Evaluation of a Binding Reaction with the Antigen 1000 nM C-terminal heptapeptide fragment of BGP (RRFYGPY: SEQ ID NO: 19) was injected onto the immobilization substrate I obtained above over 10 minutes, and the binding amount of the C-terminal heptapeptide fragment of BGP was evaluated.

Comparative Example 5

An immobilization substrate J was obtained in the same manner as in Example 5, except that, in immobilization of the complex, MBP-VH(BGP) and MBP-VL(BGP) were immobilized in this order. The binding amount of the BGP heptapeptide in the immobilization substrate J was evaluated in the same manner as in Example 5.

Evaluation

Measurement of the Binding Ratio of the BGP Heptapeptide

Based on the results obtained in Example 5 and Comparative Example 5, the binding ratio of the BGP heptapeptide was calculated and compared. Time-dependent change in binding over a period of 10 minutes from starting the addition of the BGP heptapeptide was measured using BIACORE 3000. The binding ratio of the BGP heptapeptide was obtained by dividing the binding amount of the BGP heptapeptide over the 10-minutes-period by the immobilization amount of the antibody fragments. The binding amount of the BGP heptapeptide was calculated and expressed as a relative value, assuming that the binding amount of the BGP heptapeptide in Comparative Example 5 is 1.

The results are shown in Table 14

TABLE 14

| | Immobilization substrate | BGP heptapeptide binding ratio | Immobilization amount (pg/mm$^2$) |
|---|---|---|---|
| Example 5 | I | 14.3 | 2120 |
| Comparative Example 5 | J | 1 | 2346 |

As is apparent from Table 14, even when the antigen is a low-molecular-weight molecule such as a peptide with seven residues, the reaction of a complex composed of three or more substances can be efficiently detected, and detection sensitivity and accuracy can be improved. Therefore, according to the present invention, there is provided an immobilization substrate having greater versatility that can immobilize antibodies without depending on the type of a protein even when using a low-molecular-weight antigen.

Accordingly, the present invention provides an immobilization substrate having greater versatility that can precisely detect an interaction between one type of test substance and two or more types of substances, for example, an interaction between one type of antigen and two or more types of antibody fragments, with stable binding properties.

All publications, patent applications, and technical standards mentioned in this specification are herein incorporated by reference to the same extent as if each individual publication, patent application, or technical standard was specifically and individually indicated to be incorporated by reference.

The invention claimed is:

1. A method for producing an antibody-fragment immobilizing substrate, comprising:

contacting separate antibody fragments of at least two types, the at least two types of antibody fragments being capable of recognizing the same antigen, with said antigen, to form a complex whereby each of the antibody fragments binds to said antigen, wherein said separate antibody fragments of at least two types are an antibody fragment comprising a VH-region polypeptide but not a VL-region polypeptide, and an antibody fragment comprising a VL-region polypeptide but not a VH-region polypeptide, respectively;

immobilizing the complex on a substrate via the antibody fragments in the complex; and removing the antigen from the complex to obtain the antibody-fragment-immobilizing substrate, wherein:

each of the antibody fragments are independently immobilized on the substrate in a positional relationship that allows each of the antibody fragments to bind to said antigen;

the at least two types of antibody fragments can cooperatively recognize and bind to a single molecule of said antigen, and each of the at least two types of antibody fragments has at least a part of an antigen recognition site for the same epitope on said antigen.

2. The method for producing the antibody-fragment-immobilizing substrate according to claim 1, wherein the contacting includes mixing the antibody fragments and the antigen such that the ratio of the number of antigens to the valencies of molecules formed by a combination of antibody fragments is from 0.1:1 to 10:1.

3. The method for producing the antibody-fragment-immobilizing substrate according to claim 1, wherein the removing is carried out under a condition that reduces the avidity of the antibody fragments and the antigen in the complex.

4. The method for producing the antibody-fragment-immobilizing substrate according to claim 1, wherein the antigen has only one epitope which is recognized by each of the at least two types of antibody fragments.

5. The method for producing the antibody-fragment-immobilizing substrate according to claim 1, wherein the contacting includes mixing the antibody fragments and the antigen such that the ratio of the number of antigens to the valencies of molecules formed by a combination of antibody fragments is from 0.1:1 to 1:1.

6. The method for producing the antibody-fragment-immobilizing substrate according to claim 1, wherein the contacting includes mixing the antibody fragments and the antigen such that the ratio of the number of antigens to the valencies of molecules formed by a combination of antibody fragments is from 0.1:1 to 0.3:1.

7. The method for producing the antibody-fragment-immobilizing substrate according to claim 1, wherein the contacting includes mixing the antibody fragments and the antigen such that the ratio of the number of antigens to the valencies of molecules formed by a combination of antibody fragments is from 0.5:1 to 1.5:1.

* * * * *

SEQUENCE LISTING

<160> NUMBER OF SEQ ID NOS: 19

<210> SEQ ID NO 1
<211> LENGTH: 59
<212> TYPE: DNA
<213> ORGANISM: Artificial
<220> FEATURE:
<223> OTHER INFORMATION: primer (1)

<400> SEQUENCE: 1
aaaaaaagcg gccgcggagc atcatcacca tcaccaccac caccaccact gagatccgg      59

<210> SEQ ID NO 2
<211> LENGTH: 18
<212> TYPE: DNA
<213> ORGANISM: Artificial
<220> FEATURE:
<223> OTHER INFORMATION: primer (2)

<400> SEQUENCE: 2
ccaatgctta atcagtga      18

<210> SEQ ID NO 3
<211> LENGTH: 49
<212> TYPE: DNA
<213> ORGANISM: Artificial
<220> FEATURE:
<223> OTHER INFORMATION: primer (3)

<400> SEQUENCE: 3
ctttctatgc ggcccagccg gccatggccg akgtsvagct tcaggagtc      49

<210> SEQ ID NO 4
<211> LENGTH: 34
<212> TYPE: DNA
<213> ORGANISM: Artificial
<220> FEATURE:
<223> OTHER INFORMATION: primer (4)

<400> SEQUENCE: 4
aaaaaagcgg ccgcgctcga gacggtgacc gtgg      34

<210> SEQ ID NO 5
<211> LENGTH: 45
<212> TYPE: DNA
<213> ORGANISM: Artificial
<220> FEATURE:
<223> OTHER INFORMATION: primer (5)

<400> SEQUENCE: 5
aaaaaaggcc cagccggcca tggcgtcgac ggatattttg atgac      45

<210> SEQ ID NO 6
<211> LENGTH: 36
<212> TYPE: DNA
<213> ORGANISM: Artificial
<220> FEATURE:
<223> OTHER INFORMATION: primer (6)

<400> SEQUENCE: 6
tttctcgtgc ggccgcacgt tttatttcca actttg      36

<210> SEQ ID NO 7
<211> LENGTH: 5217
<212> TYPE: DNA
<213> ORGANISM: Artificial

<220> FEATURE:
<223> OTHER INFORMATION: pET-MBP-His6

<400> SEQUENCE: 7

```
ctagaaataa ttttgtttaa ctttaagaag gagatataca tatgaaaata aaaacaggtg      60
cacgcatcct cgcattatcc gcattaacga cgatgatgtt ttccgcctcg gctctcgcca     120
aaatcgaaga aggtaaactg gtaatctgga ttaacggcga taaaggctat aacggtctcg     180
ctgaagtcgg taagaaattc gagaaagata ccggaattaa agtcaccgtt gagcatccgg     240
ataaactgga agagaaattc ccacaggttg cggcaactgg cgatggccct gacattatct     300
tctgggcaca cgaccgcttt ggtggctacg ctcaatctgg cctgttggct gaaatcaccc     360
cggacaaagc gttccaggac aagctgtatc cgtttacctg ggatgccgta cgttacaacg     420
gcaagctgat tgcttacccg atcgctgttg aagcgttatc gctgatttat aacaaagatc     480
tgctgccgaa cccgccaaaa acctgggaag atcccggc gctggataaa gaactgaaag     540
cgaaaggtaa gagcgcgctg atgttcaacc tgcaagaacc gtacttcacc tggccgctga     600
ttgctgctga cggggttat gcgttcaagt atgaaacgg caagtacgac attaaagacg     660
tgggcgtgga taacgctggc gcgaaagcgg gtctgacctt cctggttgac ctgattaaaa     720
acaaacacat gaatgcagac accgattact ccatcgcaga agctgccttt aataaaggcg     780
aaacagcgat gaccatcaac ggcccgtggg catggtccaa catcgacacc agcaaagtga     840
attatggtgt aacggtactg ccgaccttca agggtcaacc atccaaaccg ttcgttggcg     900
tgctgagcgc aggtattaac gccgccagtc gaacaaaga gctggcaaaa gagttcctcg     960
aaaactatct gctgactgat gaaggtctgg aagcggttaa taaagacaaa ccgctgggtg    1020
ccgtagcgct gaagtcttac gaggaagagt tggcgaaaga tccacgtatt gccgccacca    1080
tggaaaacgc ccagaaaggt gaaatcatgc cgaacatccc gcagatgtcc gctttctggt    1140
atgccgtgcg tactgcggtg atcaacgccg ccagcggtcg tcagactgtc gatgaagccc    1200
tgaaagacgc gcagactaat tcgagctcga acaacaacaa caataacaat aacaacaacc    1260
tcgggccggg tgcggcacac tacgtagaat tcgcggccca gccggccatg gccgactaca    1320
aagatattgt gctgacacag tctcctgctt ccttagctgt atctctgggg cagagggcca    1380
ccatctcatg cagggccagc caaagtgtca gtacatctac ctatagttat ttacactggt    1440
accaacagag accaggacag ccacccaaac tcatcaagta tgtatccaac ctagaatctg    1500
gggtccctgc caggttcagt ggcagtgggt ctgggacaga cttcacctc aacatccatc    1560 ctgtggagga ggaggatact gcaacatatt actgtcagca cagttgggag attcctccga    1620
cgttcggtgg aggcaccaag ctggaaataa aacgtgcggc cgcggtcgag caccaccacc    1680
accaccactg agatccggct gctaacaaag cccgaaagga agctgagttg gctgctgcca    1740
ccgctgagca ataactagca taaccccttg ggcctctaa acgggtcttg agggttttt     1800 tgctgaaagg aggaactata tccggattgg cgaatgggac gcgccctgta gcggcgcatt    1860
aagcgcggcg ggtgtggtgg ttacgcgcag cgtgaccgct acacttgcca gcgccctagc    1920
gcccgctcct ttcgctttct tcccttcctt tctcgccacg ttcgccggct ttccccgtca    1980
agctctaaat cggggctcc ctttagggtt ccgatttagt gctttacggc acctcgaccc    2040
caaaaaactt gattagggtg atggttcacg tagtgggcca tcgccctgat agacggtttt    2100
tcgccctttg acgttggagt ccacgttctt taatagtgga ctcttgttcc aaactggaac    2160
aacactcaac cctatctcgg tctattcttt tgatttataa gggattttgc cgatttcggc    2220
```

-continued

```
ctattggtta aaaaatgagc tgatttaaca aaaatttaac gcgaattta  acaaaatatt  2280 aacgtttaca atttcaggtg gcacttttcg gggaaatgtg cgcggaaccc ctatttgttt  2340 attttctaa  atacattcaa atatgtatcc gctcatgaga caataaccct gataaatgct  2400
tcaataatat tgaaaaagga agagtatgag tattcaacat ttccgtgtcg cccttattcc  2460
cttttttgcg gcattttgcc ttcctgtttt tgctcaccca gaaacgctgg tgaaagtaaa  2520
agatgctgaa gatcagttgg gtgcacgagt gggttacatc gaactggatc tcaacagcgg  2580
taagatcctt gagagttttc gccccgaaga acgttttcca atgatgagca cttttaaagt  2640
tctgctatgt ggcgcggtat tatcccgtat tgacgccggg caagagcaac tcggtcgccg  2700
catacactat tctcagaatg acttggttga gtactcacca gtcacagaaa agcatcttac  2760
ggatggcatg acagtaagag aattatgcag tgctgccata accatgagtg ataacactgc  2820
ggccaactta cttctgacaa cgatcggagg accgaaggag ctaaccgctt ttttgcacaa  2880
catgggggat catgtaactc gccttgatcg ttgggaaccg gagctgaatg aagccatacc  2940
aaacgacgag cgtgacacca cgatgcctgc agcaatggca acaacgttgc gcaaactatt  3000
aactggcgaa ctacttactc tagcttcccg gcaacaatta atagactgga tggaggcgga  3060
taaagttgca ggaccacttc tgcgctcggc ccttccggct ggctggttta ttgctgataa  3120
atctggagcc ggtgagcgtg ggtctcgcgg tatcattgca gcactggggc cagatggtaa  3180
gccctcccgt atcgtagtta tctacacgac ggggagtcag gcaactatgg atgaacgaaa  3240
tagacagatc gctgagatag gtgcctcact gattaagcat tggtaactgt cagaccaagt  3300
ttactcatat atactttaga ttgatttaaa acttcatttt taatttaaaa ggatctaggt  3360
gaagatcctt tttgataatc tcatgaccaa aatcccttaa cgtgagtttt cgttccactg  3420
agcgtcagac cccgtagaaa agatcaaagg atcttcttga tccttttttt ttctgcgcgt  3480
aatctgctgc ttgcaaacaa aaaaaccacc gctaccagcg gtggtttgtt tgccggatca  3540
agagctacca actctttttc cgaaggtaac tggcttcagc agagcgcaga taccaaatac  3600
tgtccttcta gtgtagccgt agttaggcca ccacttcaag aactctgtag caccgcctac  3660
atacctcgct ctgctaatcc tgttaccagt ggctgctgcc agtggcgata agtcgtgtct  3720
taccgggttg gactcaagac gatagttacc ggataaggcg cagcggtcgg gctgaacggg  3780
gggttcgtgc acacagccca gcttggagcg aacgacctac accgaactga gatacctaca  3840
gcgtgagcta tgagaaagcg ccacgcttcc cgaagggaga aaggcggaca ggtatccggt  3900
aagcggcagg gtcggaacag gagagcgcac gagggagctt ccagggggaa acgcctggta  3960
tctttatagt cctgtcgggt ttcgccacct ctgacttgag cgtcgatttt tgtgatgctc  4020 gtcaggggg  cggagcctat ggaaaaacgc cagcaacgcg ccttttac  ggttcctggc  4080 cttttgctgg ccttttgctc acatgttctt tcctgcgtta tcccctgatt ctgtggataa  4140
ccgtattacc gcctttgagt gagctgatac cgctcgccgc agccgaacga ccgagcgcag  4200
cgagtcagtg agcgaggaag cggaagagcg cctgatgcgg tattttctcc ttacgcatct  4260
gtgcggtatt tcacaccgca tatatggtgc actctcagta caatctgctc tgatgccgca  4320
tagttaagcc agtatacact ccgctatcgc tacgtgactg ggtcatggct gcgccccgac  4380
acccgccaac acccgctgac gcgccctgac gggcttgtct gctcccggca tccgcttaca  4440
gacaagctgt gaccgtctcc gggagctgca tgtgtcagag gttttcaccg tcatcaccga  4500
aacgcgcgag gcagctgcgg taagctcat  cagcgtggtc gtgaagcgat tcacagatgt  4560
ctgcctgttc atccgcgtcc agctcgttga gtttctccag aagcgttaat gtctggcttc  4620
```

```
tgataaagcg ggccatgtta agggcggttt tttcctgttt ggtcactgat gcctccgtgt      4680 aaggggatt tctgttcatg ggggtaatga taccgatgaa acgagagagg atgctcacga       4740
tacgggttac tgatgatgaa catgcccggt tactggaacg ttgtgagggt aaacaactgg      4800
cggtatggat gcgcgggac cagagaaaaa tcactcaggg tcaatgccag cgcttcgtta       4860
atacagatgt aggtgttcca cagggtagcc agcagcatcc tgcgatgcag atccggaaca     4920
taatggtgca gggcgctgac ttccgcgttt ccagactta cgaaacacgg aaaccgaaga       4980
ccattcatgt tgttgctcag gtcgcagacg ttttgcagca gcagtcgctt cacgttcgct     5040
cgcgtatcgg tgattcattc tgctaaccag taaggcaacc ccgccagcct agccgggtcc     5100
tcaacgacag gagcacgatc atgcgcaccc gtggccagga cccaacgctg cccgagatct     5160
cgatcccgcg aaattaatac gactcactat agggagacca caacggtttc cctctag         5217

<210> SEQ ID NO 8
<211> LENGTH: 840
<212> TYPE: DNA
<213> ORGANISM: Artificial
<220> FEATURE:
<223> OTHER INFORMATION: pIT2-LxE16
<220> FEATURE:
<221> NAME/KEY: CDS
<222> LOCATION: (29)..(838)

<400> SEQUENCE: 8
caaattctat ttcaaggaga cagtcata atg aaa tac cta ttg cct acg gca             52
                            Met Lys Tyr Leu Leu Pro Thr Ala
                              1               5 gcc gct gga ttg tta tta ctc gcg gcc cag ccg gcc atg gcc gag gtg          100
Ala Ala Gly Leu Leu Leu Leu Ala Ala Gln Pro Ala Met Ala Glu Val
       10                  15                  20 cag ctt cag gag tca gga cct agc ctc gtg aaa cct tct cag act ctg          148
Gln Leu Gln Glu Ser Gly Pro Ser Leu Val Lys Pro Ser Gln Thr Leu
25                  30                  35                  40 tcc ctc acc tgt tct gtc act ggc gac tcc atc acc agg ggt tac tgg          196
Ser Leu Thr Cys Ser Val Thr Gly Asp Ser Ile Thr Arg Gly Tyr Trp
                45                  50                  55 agc tgg atc cgg aaa tcc cca gga aat aaa ctt gag tac atg ggg tac          244
Ser Trp Ile Arg Lys Ser Pro Gly Asn Lys Leu Glu Tyr Met Gly Tyr
            60                  65                  70 ata agc tac agt ggt agc act ttc tac aat cca tct ctc aaa agt cga          292
Ile Ser Tyr Ser Gly Ser Thr Phe Tyr Asn Pro Ser Leu Lys Ser Arg
        75                  80                  85 atc tcc atc act cga gac aca ttc aag aac cag ctc tac ctg cag ttg          340
Ile Ser Ile Thr Arg Asp Thr Phe Lys Asn Gln Leu Tyr Leu Gln Leu
    90                  95                 100 aat tct gtg act act gag gac aca gcc aca tat tat tgt gca gag tac          388
Asn Ser Val Thr Thr Glu Asp Thr Ala Thr Tyr Tyr Cys Ala Glu Tyr
105                 110                 115                 120 gac ggg act tac tgg ggc caa ggg acc acg gtc acc gtc tcg agc ggt          436
Asp Gly Thr Tyr Trp Gly Gln Gly Thr Thr Val Thr Val Ser Ser Gly
                125                 130                 135 gga ggc ggt tca ggc gga ggt ggc agc ggc ggt ggc ggg tcg acg gat          484
Gly Gly Gly Ser Gly Gly Gly Gly Ser Gly Gly Gly Gly Ser Thr Asp
            140                 145                 150 att ttg atg acc cag act cca gcc acc ctg tct gtg act cca gga gat          532
Ile Leu Met Thr Gln Thr Pro Ala Thr Leu Ser Val Thr Pro Gly Asp
        155                 160                 165
```

```
agc gtc agt ctt tcc tgc agg gcc agc caa agt att ggc aac aac cta    580
Ser Val Ser Leu Ser Cys Arg Ala Ser Gln Ser Ile Gly Asn Asn Leu
    170                 175                 180 cac tgg ttt caa caa aaa tca cat gag tct cca agg ctt ctc atc aag    628
His Trp Phe Gln Gln Lys Ser His Glu Ser Pro Arg Leu Leu Ile Lys
185                 190                 195                 200 tat gct tcc cag tcc atc tct ggg atc ccc tcc agg ttc agt ggc agt    676
Tyr Ala Ser Gln Ser Ile Ser Gly Ile Pro Ser Arg Phe Ser Gly Ser
                205                 210                 215 gga tca ggg aca gat ttc act ctc agt atc aac act gtg gag act gaa    724
Gly Ser Gly Thr Asp Phe Thr Leu Ser Ile Asn Thr Val Glu Thr Glu
            220                 225                 230 gat ttt gga atg tat ttc tgt caa cag agt aac agc tgg ccg tac acg    772
Asp Phe Gly Met Tyr Phe Cys Gln Gln Ser Asn Ser Trp Pro Tyr Thr
        235                 240                 245 ttc gga ggg ggg aca aag ttg gaa ata aaa cgt gcg gcc gca cat cat    820
Phe Gly Gly Gly Thr Lys Leu Glu Ile Lys Arg Ala Ala Ala His His
    250                 255                 260 cat cac cat cac ggg gcc gc                                         840
His His His His Gly Ala
265                 270

<210> SEQ ID NO 9
<211> LENGTH: 270
<212> TYPE: PRT
<213> ORGANISM: Artificial
<220> FEATURE:
<223> OTHER INFORMATION: Synthetic Polypeptide

<400> SEQUENCE: 9

Met Lys Tyr Leu Leu Pro Thr Ala Ala Ala Gly Leu Leu Leu Leu Ala
1               5                   10                  15

Ala Gln Pro Ala Met Ala Glu Val Gln Leu Gln Glu Ser Gly Pro Ser
            20                  25                  30

Leu Val Lys Pro Ser Gln Thr Leu Ser Leu Thr Cys Ser Val Thr Gly
        35                  40                  45

Asp Ser Ile Thr Arg Gly Tyr Trp Ser Trp Ile Arg Lys Ser Pro Gly
    50                  55                  60

Asn Lys Leu Glu Tyr Met Gly Tyr Ile Ser Tyr Ser Gly Ser Thr Phe
65                  70                  75                  80

Tyr Asn Pro Ser Leu Lys Ser Arg Ile Ser Ile Thr Arg Asp Thr Phe
                85                  90                  95

Lys Asn Gln Leu Tyr Leu Gln Leu Asn Ser Val Thr Thr Glu Asp Thr
            100                 105                 110

Ala Thr Tyr Tyr Cys Ala Glu Tyr Asp Gly Thr Tyr Trp Gly Gln Gly
        115                 120                 125

Thr Thr Val Thr Val Ser Gly Gly Gly Ser Gly Gly Gly Gly
    130                 135                 140

Ser Gly Gly Gly Gly Ser Thr Asp Ile Leu Met Thr Gln Thr Pro Ala
145                 150                 155                 160

Thr Leu Ser Val Thr Pro Gly Asp Ser Val Ser Leu Ser Cys Arg Ala
                165                 170                 175

Ser Gln Ser Ile Gly Asn Asn Leu His Trp Phe Gln Gln Lys Ser His
            180                 185                 190

Glu Ser Pro Arg Leu Leu Ile Lys Tyr Ala Ser Gln Ser Ile Ser Gly
        195                 200                 205

Ile Pro Ser Arg Phe Ser Gly Ser Gly Ser Gly Thr Asp Phe Thr Leu
    210                 215                 220
```

```
Ser Ile Asn Thr Val Glu Thr Glu Asp Phe Gly Met Tyr Phe Cys Gln
225                 230                 235                 240

Gln Ser Asn Ser Trp Pro Tyr Thr Phe Gly Gly Gly Thr Lys Leu Glu
            245                 250                 255

Ile Lys Arg Ala Ala Ala His His His His His His Gly Ala
        260                 265                 270

<210> SEQ ID NO 10
<211> LENGTH: 341
<212> TYPE: DNA
<213> ORGANISM: Artificial
<220> FEATURE:
<223> OTHER INFORMATION: VH(HEL)

<400> SEQUENCE: 10
atggccgagg tgcagcttca ggagtcagga cctagcctcg tgaaaccttc tcagactctg      60
tccctcacct gttctgtcac tggcgactcc atcaccaggg gttactggag ctggatccgg     120
aaatccccag gaaataaact tgagtacatg ggtacataa ctacagtgg tagcactttc      180 tacaatccat ctctcaaaag tcgaatctcc atcactcgag acacattcaa gaaccagctc     240
tacctgcagt tgaattctgt gactactgag gacacagcca catattattg tgcagagtac     300
gacgggactt actggggcca agggaccacg gtcaccgtct c                         341

<210> SEQ ID NO 11
<211> LENGTH: 330
<212> TYPE: DNA
<213> ORGANISM: Artificial
<220> FEATURE:
<223> OTHER INFORMATION: VL(HEL)

<400> SEQUENCE: 11
tcgacggata ttttgatgac ccagactcca gccaccctgt ctgtgactcc aggagatagc      60
gtcagtcttt cctgcagggc cagccaaagt attggcaaca acctacactg gtttcaacaa     120
aaatcacatg agtctccaag gcttctcatc aagtatgctt cccagtccat ctctgggatc     180
ccctccaggt tcagtggcag tggatcaggg acagatttca ctctcagtat caacactgtg     240
gagactgaag attttggaat gtatttctgt caacagagta cagctggcc gtacacgttc      300 ggagggggga caaagttgga aataaaacgt                                      330

<210> SEQ ID NO 12
<211> LENGTH: 551
<212> TYPE: PRT
<213> ORGANISM: Artificial
<220> FEATURE:
<223> OTHER INFORMATION: MBP-VH(HEL)-His10

<400> SEQUENCE: 12

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80
```

```
Asp Gly Pro Asp Ile Phe Trp Ala His Asp Arg Phe Gly Tyr
             85                  90                  95

Ala Gln Ser Gly Leu Leu Ala Glu Ile Thr Pro Asp Lys Ala Phe Gln
        100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
                260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
        290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
        370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Pro Gly Ala Ala His Tyr Val Glu
                405                 410                 415

Phe Ala Ala Gln Pro Ala Met Ala Asp Val Glu Leu Gln Glu Ser Gly
            420                 425                 430

Pro Ser Leu Val Lys Pro Ser Gln Thr Leu Ser Leu Thr Cys Ser Val
            435                 440                 445

Thr Gly Asp Ser Ile Thr Arg Gly Tyr Trp Ser Trp Ile Arg Lys Phe
        450                 455                 460

Pro Gly Asn Lys Leu Glu Tyr Met Gly Tyr Ile Ser Tyr Ser Gly Ser
465                 470                 475                 480

Thr Phe Tyr Asn Pro Ser Leu Lys Ser Arg Ile Ser Ile Thr Arg Asp
            485                 490                 495
```

```
Thr Phe Lys Asn Gln Leu Tyr Leu Gln Leu Asn Ser Val Thr Thr Glu
                500                 505                 510

Asp Thr Ala Thr Tyr Tyr Cys Ala Glu Tyr Asp Gly Thr Tyr Trp Gly
            515                 520                 525

Gln Gly Thr Thr Val Thr Val Ser Ser Ala Ala Ala Glu His His His
        530                 535                 540

His His His His His His
545                 550

<210> SEQ ID NO 13
<211> LENGTH: 548
<212> TYPE: PRT
<213> ORGANISM: Artificial
<220> FEATURE:
<223> OTHER INFORMATION: MBP-VL(HEL)-His10

<400> SEQUENCE: 13

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
130                 135                 140

Lys Asp Leu Leu Pro Asn Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
290                 295                 300
```

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu
            325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
            370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Pro Gly Ala Ala His Tyr Val Glu
                405                 410                 415

Phe Ala Ala Gln Pro Ala Met Ala Ser Thr Asp Ile Leu Met Thr Gln
            420                 425                 430

Thr Pro Ala Thr Leu Ser Val Thr Pro Gly Asp Ser Val Ser Leu Ser
            435                 440                 445

Cys Arg Ala Ser Gln Ser Ile Gly Asn Asn Leu His Trp Phe Gln Gln
450                 455                 460

Lys Ser His Glu Ser Pro Arg Leu Leu Ile Lys Tyr Ala Ser Gln Ser
465                 470                 475                 480

Ile Ser Gly Ile Pro Ser Arg Phe Ser Gly Ser Gly Thr Asp
            485                 490                 495

Phe Thr Leu Ser Ile Asn Thr Val Glu Thr Glu Asp Phe Gly Met Tyr
            500                 505                 510

Phe Cys Gln Gln Ser Asn Ser Trp Pro Tyr Thr Phe Gly Gly Gly Thr
            515                 520                 525

Lys Leu Glu Ile Lys Arg Ala Ala Ala Glu His His His His His
            530                 535                 540

His His His His
545

<210> SEQ ID NO 14
<211> LENGTH: 134
<212> TYPE: PRT
<213> ORGANISM: Artificial
<220> FEATURE:
<223> OTHER INFORMATION: VH(HEL)-His6

<400> SEQUENCE: 14

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Arg Gly
            20                  25                  30

Tyr Trp Ser Trp Ile Arg Lys Phe Pro Gly Asn Lys Leu Glu Tyr Met
            35                  40                  45

Gly Tyr Ile Ser Tyr Ser Gly Ser Thr Phe Tyr Asn Pro Ser Leu Lys
        50                  55                  60

Ser Arg Ile Ser Ile Thr Arg Asp Thr Phe Lys Asn Gln Leu Tyr Leu
65                  70                  75                  80

Gln Leu Asn Ser Val Thr Thr Glu Asp Thr Ala Thr Tyr Tyr Cys Ala
            85                  90                  95

Glu Tyr Asp Gly Thr Tyr Trp Gly Gln Gly Thr Thr Val Thr Val His
            100                 105                 110

His His His His His Gly Ala Ala Glu Gln Lys Leu Ile Ser Glu Glu
              115                 120                 125

Asp Leu Asn Gly Ala Ala
        130

<210> SEQ ID NO 15
<211> LENGTH: 348
<212> TYPE: DNA
<213> ORGANISM: Artificial
<220> FEATURE:
<223> OTHER INFORMATION: VH(BGP)
<220> FEATURE:
<221> NAME/KEY: CDS
<222> LOCATION: (1)..(348)

<400> SEQUENCE: 15

```
gag gta cag ctg gag gag tct ggg gct gag ttt gtg aag gct ggg gct    48
Glu Val Gln Leu Glu Glu Ser Gly Ala Glu Phe Val Lys Ala Gly Ala
1               5                   10                  15 tca gtg aag ctg tcc tgc aag act tct ggc tac acc ttc aac aac tac    96
Ser Val Lys Leu Ser Cys Lys Thr Ser Gly Tyr Thr Phe Asn Asn Tyr
            20                  25                  30 tgg att cac tgg gtc aaa cag agc cca gga caa ggc ctt gaa tgg atc   144
Trp Ile His Trp Val Lys Gln Ser Pro Gly Gln Gly Leu Glu Trp Ile
        35                  40                  45 gga gaa att gat ccc tct gat ggt tat tct aac tac aat caa aaa ttc   192
Gly Glu Ile Asp Pro Ser Asp Gly Tyr Ser Asn Tyr Asn Gln Lys Phe
    50                  55                  60 aag ggc aag gcc aca ttg act gtg gac aag tcc tcc agc act gcc tac   240
Lys Gly Lys Ala Thr Leu Thr Val Asp Lys Ser Ser Ser Thr Ala Tyr
65                  70                  75                  80 atg cac ctc aac agt ctg act tct gag gac tct gcg gtc tat tat tgt   288
Met His Leu Asn Ser Leu Thr Ser Glu Asp Ser Ala Val Tyr Tyr Cys
                85                  90                  95 aca agc agc act tcg gta gga ggt tcc tgg ggc caa ggg acc acg gtc   336
Thr Ser Ser Thr Ser Val Gly Gly Ser Trp Gly Gln Gly Thr Thr Val
            100                 105                 110 acc gtc tcg agc                                                    348
Thr Val Ser Ser
        115
```

<210> SEQ ID NO 16
<211> LENGTH: 116
<212> TYPE: PRT
<213> ORGANISM: Artificial
<220> FEATURE:
<223> OTHER INFORMATION: Synthetic Polypeptide

<400> SEQUENCE: 16

Glu Val Gln Leu Glu Glu Ser Gly Ala Glu Phe Val Lys Ala Gly Ala
1               5                   10                  15

Ser Val Lys Leu Ser Cys Lys Thr Ser Gly Tyr Thr Phe Asn Asn Tyr
            20                  25                  30

Trp Ile His Trp Val Lys Gln Ser Pro Gly Gln Gly Leu Glu Trp Ile
        35                  40                  45

Gly Glu Ile Asp Pro Ser Asp Gly Tyr Ser Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Tyr Cys
                85                  90                  95

Thr Ser Ser Thr Ser Val Gly Gly Ser Trp Gly Gln Gly Thr Thr Val
              100                 105                 110

Thr Val Ser Ser
        115

<210> SEQ ID NO 17
<211> LENGTH: 544
<212> TYPE: PRT
<213> ORGANISM: Artificial
<220> FEATURE:
<223> OTHER INFORMATION: MBP-VH(BGP)

<400> SEQUENCE: 17

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

-continued

```
Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Pro Gly Ala Ala His Tyr Val Glu
                405                 410                 415

Phe Ala Ala Gln Pro Ala Glu Val Gln Leu Glu Glu Ser Gly Ala Glu
            420                 425                 430

Phe Val Lys Ala Gly Ala Ser Val Lys Leu Ser Cys Lys Thr Ser Gly
        435                 440                 445

Tyr Thr Phe Asn Ser Tyr Trp Ile His Trp Ile Lys Gln Ser Pro Gly
    450                 455                 460

Gln Gly Leu Glu Trp Ile Gly Glu Ile Asp Pro Ser Asp Gly Tyr Thr
465                 470                 475                 480

Asn Tyr Asn Gln Lys Phe Lys Gly Lys Ala Thr Leu Thr Val Asp Lys
                485                 490                 495

Ser Ser Ser Thr Ala Tyr Met Arg Leu Asn Ser Leu Thr Ser Glu Asp
            500                 505                 510

Ser Ala Val Tyr Tyr Cys Thr Ser Ser Thr Ser Val Gly Gly Ser Trp
        515                 520                 525

Gly Gln Gly Thr Thr Val Thr Val Ser Ser His His His His
    530                 535                 540

<210> SEQ ID NO 18
<211> LENGTH: 555
<212> TYPE: PRT
<213> ORGANISM: Artificial
<220> FEATURE:
<223> OTHER INFORMATION: MBP-VL(BGP)

<400> SEQUENCE: 18

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160
```

Leu Asp Lys Glu Leu Lys Ala Lys Gly Lys Ser Ala Leu Met Phe Asn
165                 170                 175

Leu Gln Glu Pro Tyr Phe Thr Trp Pro Leu Ile Ala Ala Asp Gly Gly
        180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
                260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Ile Glu Gly Arg Ile Ser Glu Phe
                405                 410                 415

Ala Ser Thr Asp Ile Glu Leu Thr Gln Ser Pro Leu Ser Leu Pro Val
            420                 425                 430

Ser Leu Gly Asp Gln Ala Ser Ile Ser Cys Thr Ser Ser Gln Ser Leu
435                 440                 445

Leu His Ser Asn Gly Asp Thr Tyr Leu His Trp Tyr Leu Gln Lys Pro
450                 455                 460

Gly Gln Ser Pro Lys Leu Leu Ile Tyr Thr Leu Ser Asn Arg Phe Ser
465                 470                 475                 480

Gly Val Pro Asp Arg Phe Ser Gly Ser Gly Ser Gly Thr Asp Phe Thr
            485                 490                 495

Leu Lys Ile Ser Arg Val Glu Ala Ala Asp Leu Gly Ile Tyr Phe Cys
            500                 505                 510

Ser Gln Thr Thr His Val Pro Tyr Thr Phe Gly Gly Gly Thr Lys Leu
            515                 520                 525

Glu Ile Lys Arg His His His His His His Gly Ala Ala Glu Gln Lys
530                 535                 540

Leu Ile Ser Glu Glu Asp Leu Asn Gly Ala Ala
545                 550                 555

<210> SEQ ID NO 19
<211> LENGTH: 7
<212> TYPE: PRT

```
<213> ORGANISM: Artificial
<220> FEATURE:
<223> OTHER INFORMATION: BGP fragment

<400> SEQUENCE: 19

Arg Arg Phe Tyr Gly Pro Tyr
1               5
```